United States Patent
Pothoulakis et al.

(10) Patent No.: US 10,233,463 B2
(45) Date of Patent: Mar. 19, 2019

(54) NEUROTENSIN-INDUCED TUMOR FORMATION IS REGULATED BY MICRO RNA 133A-AFTIPHILIN-DEPENDENT RECEPTOR RECYCLING

(71) Applicant: THE REGENTS OF THE UNIVERSITY OF CALIFORNIA, Oakland, CA (US)

(72) Inventors: Charalabos Pothoulakis, Los Angeles, CA (US); Dimitrios Iliopoulos, Los Angeles, CA (US); Ka Man Law, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 34 days.

(21) Appl. No.: 15/282,694

(22) Filed: Sep. 30, 2016

(65) Prior Publication Data
US 2017/0088857 A1 Mar. 30, 2017

Related U.S. Application Data

(62) Division of application No. 14/891,961, filed as application No. PCT/US2014/038624 on May 19, 2014, now abandoned.
(Continued)

(51) Int. Cl.
*A61K 48/00* (2006.01)
*C12N 15/11* (2006.01)
*C07H 21/02* (2006.01)
*C07H 21/04* (2006.01)
*C12N 15/86* (2006.01)
(Continued)

(52) U.S. Cl.
CPC .......... *C12N 15/86* (2013.01); *A61K 38/1709* (2013.01); *C07K 14/47* (2013.01); *C12N 15/113* (2013.01); *C12N 15/1135* (2013.01); *C12Q 1/6883* (2013.01); *C12Q 1/6886* (2013.01); *A61K 38/00* (2013.01); *C12N 2310/11* (2013.01); *C12N 2310/113* (2013.01); *C12N 2310/14* (2013.01); *C12N 2310/141* (2013.01); *C12N 2310/3231* (2013.01);
(Continued)

(58) Field of Classification Search
CPC ..... A61K 31/7105; C12N 15/113; C12Q 1/68
See application file for complete search history.

(56) References Cited

U.S. PATENT DOCUMENTS

2009/0053169 A1* 2/2009 Castillo .............. A61K 31/7105
424/85.2
2011/0117111 A1* 5/2011 Kwon ................... C12N 15/111
424/172.1
(Continued)

OTHER PUBLICATIONS

Care et al., MicroRNA-133 controls cardiac hypertrophy, Nature Medicine, vol. 13(5):613-618 (May 2007).*
(Continued)

*Primary Examiner* — Terra C Gibbs
(74) *Attorney, Agent, or Firm* — Karen S. Canady; canady + lortz LLP

(57) ABSTRACT

This application discloses methods of treating, preventing, and diagnosing colorectal cancer and IBD in a subject comprising administering an effective dose of antisense miR-133α or AFTPH to the subject or detecting expression levels of miR-133α and AFTPH.

13 Claims, 15 Drawing Sheets

Specification includes a Sequence Listing.

Related U.S. Application Data

(60) Provisional application No. 61/824,603, filed on May 17, 2013.

(51) Int. Cl.

| | | |
|---|---|---|
| *C12N 15/113* | (2010.01) | |
| *A61K 38/17* | (2006.01) | |
| *C12Q 1/6883* | (2018.01) | |
| *C12Q 1/6886* | (2018.01) | |
| *C07K 14/47* | (2006.01) | |
| *A61K 38/00* | (2006.01) | |

(52) U.S. Cl.
CPC .............. *C12N 2320/30* (2013.01); *C12N 2740/15043* (2013.01); *C12Q 2600/158* (2013.01); *C12Q 2600/178* (2013.01)

(56) References Cited

U.S. PATENT DOCUMENTS

| | | |
|---|---|---|
| 2013/0143764 A1 | 6/2013 | Ogier-Denis et al. |
| 2013/0225440 A1 | 8/2013 | Friedman et al. |

OTHER PUBLICATIONS

Stenvang et al., Inhibition of microRNA function by antimiR oligonucleotides, Silence, vol. 3(1):1-17 (Jan. 9, 2012).*
Bader et al., The Promise of MicroRNA Replacement Therapy, Cancer Res, vol. 70(18):7027-30 (Aug. 31, 2010).*
Necela et al., Differential Expression of MicroRNAs in Tumors from Chronically Inflamed or Genetic (APCMin/+) Models of Colon Cancer, PLoS One, 6(4):e18501 (Apr. 12, 2011).*
Li et al., microRNA expression profiles in human colorectal cancers with brain metastases, Oncology Letters, vol. 3:346-350 (Nov. 29, 2011).*
Luo et al., Identification and Evaluation of Plasma MicroRNAs for Early Detection of Colorectal Cancer, PLoS One, vol. 8(5):e62880, 9 pages, doi:10.1371/journal.pone.0062880 (May 14, 2013).*
Wu et al., MicroRNA in colorectal cancer; from benchtop to bedside, Carcinogenesis, vol. 32(2):247-253 (Nov. 16, 2010).*
Wahid et al., MicroRNAs: Synthesis, mechanism, function, and recent clinical trials, Biochimica et Biophysica Acta, vol. 1803:1231-1243 (Jul. 7, 2010).*
Triantafillidis et al., Colorectal Cancer and Inflammatory Bowel Disease: Epidemiology, Risk Factors, Mechanisms of Carcinogenesis and Prevention Strategies, Anticancer Research, vol. 29:2727-2738 (2009).*
Dyson et al., Colorectal cancer in inflammatory bowel disease: What is the real magnitude of risk?, World J. Gastroenterol., vol. 18(29):3839-3848 (Aug. 2012).*
Soroosh et al. (Am J. Physiol. Gastrointest Liver Physiol. 2018 vol. 314:G256-G262).*
Arndt, Greg M. et al. "Characterization of global microRNA expression reveals oncogenic potential of miR-145 in metastatic colorectal cancer", BMC Cancer 2009, 9:374.
Coskun, Mehmet et al. "MicroRNAs in inflammatory bowel disease—pathogenesis, diagnostics and therapeutics", World J Gastroenterol Sep. 14, 2012; 18(34): 4629-4634.
Law, Ivy Ka Man et al. "Neurotensin-regulated miR-133α is involved in proinflammatory signalling in human colonic epithelial cells and in experimental colitis", Gut 2015;64:1095-1104.
International Search Report & Written Opinion dated Sep. 12, 2014, for corresponding application PCT/US2014/038624 (WO2014186799), filed May 19, 2014.
International Search Report & Written Opinion dated Jan. 14, 2015, for application PCT/US2014/055493 (WO2015038960), filed Sep. 12, 2014.
MIR133A1, Gene ID: 406922, microRNA 133a-1 [*Homo sapiens* (human)], ncbi.nlm.nih.gov, 5 pages (Apr. 2016), also available at http://www.ncbi.nlm.nih.gov/gene/406922 (last visited Apr. 13, 2016).
Micro RNA 133A1, ID No. 610254, omim.org, 3 pages (created Jul. 13, 2006), also available at http://omim.org/entry/610254 (last visited Apr. 13, 2016).
Luo et al., Identification and Evaluation of plasma MicroRNAs for Early detection of Colorectal Cancer, PLoS One, vol. 8(5):e62880, 9 pages (May 14, 2013).
Li et al., microRNA expression profiles in human colorectal cancers with brain metastases, Oncology Letters, vol. 3:346-350 (online Nov. 29, 2011).

\* cited by examiner

FIGURE 13A-B
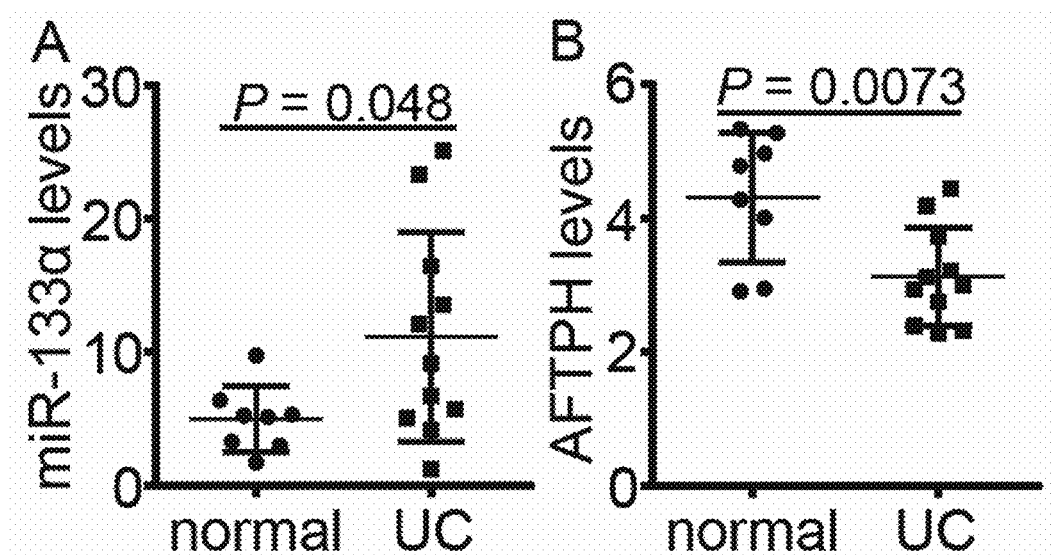
FIGURE 14
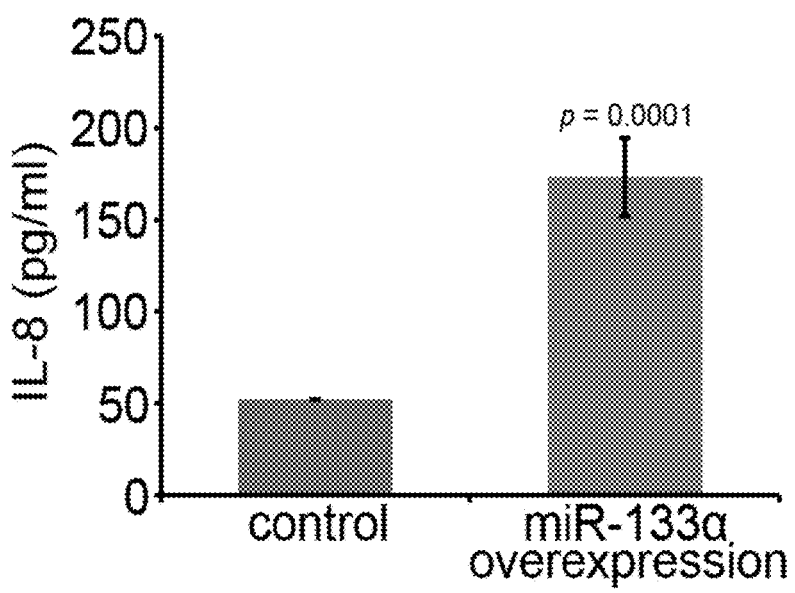

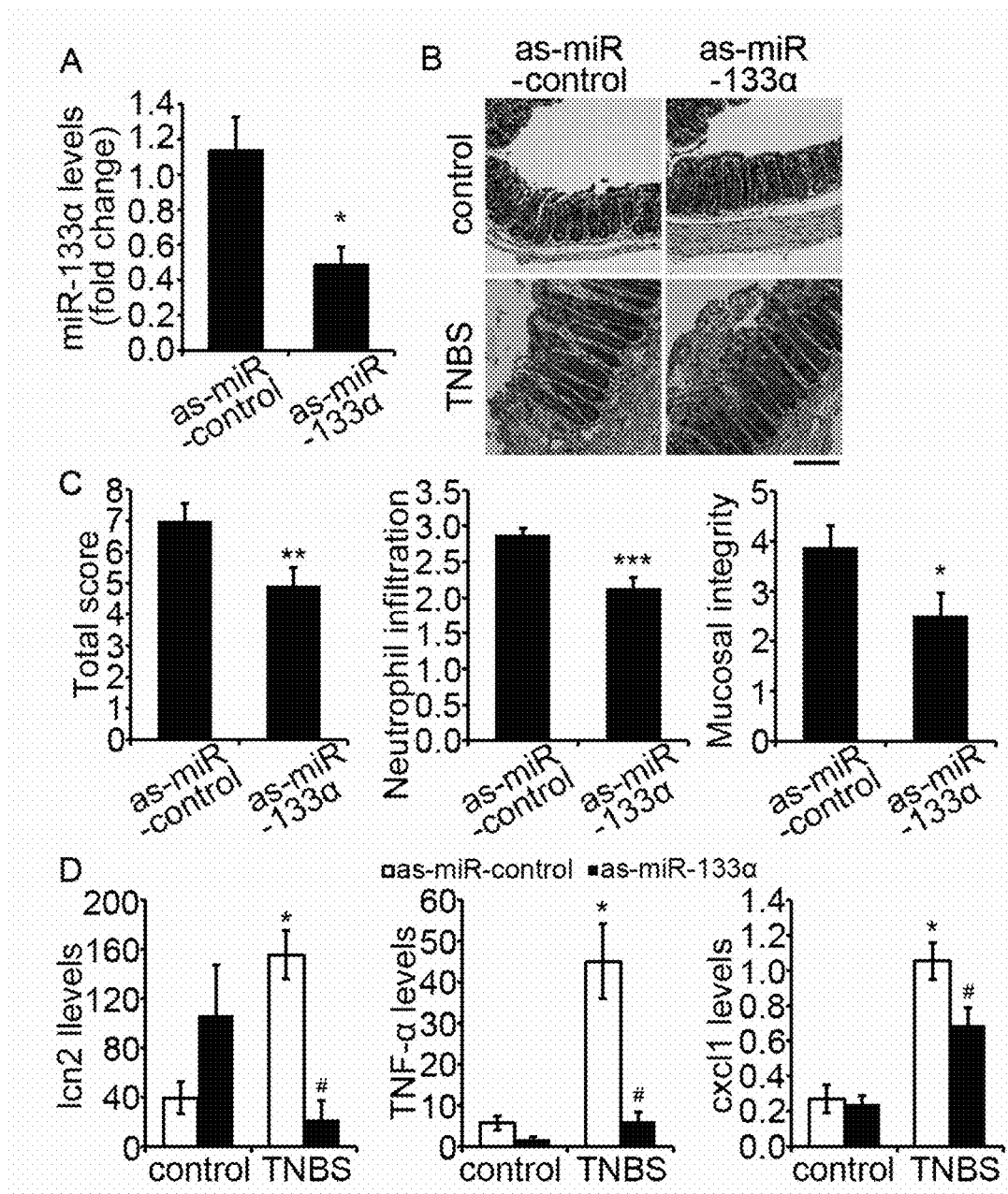
FIGURE 17A-D

```
                        SEQUENCE LISTING

<160> NUMBER OF SEQ ID NOS: 16

<210> SEQ ID NO 1
<211> LENGTH: 7
<212> TYPE: RNA
<213> ORGANISM: Homo sapiens

<400> SEQUENCE: 1 ggaccaa                                                                 7

<210> SEQ ID NO 2
<211> LENGTH: 7
<212> TYPE: RNA
<213> ORGANISM: Pan troglodytes

<400> SEQUENCE: 2 ggaccaa                                                                 7

<210> SEQ ID NO 3
<211> LENGTH: 7
<212> TYPE: RNA
<213> ORGANISM: Mus musculus

<400> SEQUENCE: 3 ggaccaa                                                                 7

<210> SEQ ID NO 4
<211> LENGTH: 7
<212> TYPE: RNA
<213> ORGANISM: Canis familiaris

<400> SEQUENCE: 4 ggaccaa                                                                 7

<210> SEQ ID NO 5
<211> LENGTH: 7
<212> TYPE: RNA
<213> ORGANISM: Felis catus

<400> SEQUENCE: 5 ggaccaa                                                                 7

<210> SEQ ID NO 6
<211> LENGTH: 7
<212> TYPE: RNA
<213> ORGANISM: Bos taurus

<400> SEQUENCE: 6 ggaccaa                                                                 7

<210> SEQ ID NO 7
<211> LENGTH: 7
<212> TYPE: RNA
<213> ORGANISM: unknown
<220> FEATURE:
<223> OTHER INFORMATION: Armadillo

<400> SEQUENCE: 7
```

-continued

```
ggaccaa                                                                   7

<210> SEQ ID NO 8
<211> LENGTH: 7
<212> TYPE: RNA
<213> ORGANISM: Gallus gallus

<400> SEQUENCE: 8 ggaccaa                                                                   7

<210> SEQ ID NO 9
<211> LENGTH: 18
<212> TYPE: RNA
<213> ORGANISM: homo sapiens

<400> SEQUENCE: 9
auucagagaa ggaccaaa                                                      18

<210> SEQ ID NO 10
<211> LENGTH: 18
<212> TYPE: RNA
<213> ORGANISM: homo sapiens

<400> SEQUENCE: 10
accaacuucc ccugguuu                                                      18

<210> SEQ ID NO 11
<211> LENGTH: 36
<212> TYPE: DNA
<213> ORGANISM: Artificial
<220> FEATURE:
<223> OTHER INFORMATION: primer

<400> SEQUENCE: 11
ccgctcgagt ttcaaagaaa ttagttcaaa gcttaa                                  36

<210> SEQ ID NO 12
<211> LENGTH: 30
<212> TYPE: DNA
<213> ORGANISM: artificial
<220> FEATURE:
<223> OTHER INFORMATION: primer

<400> SEQUENCE: 12
cccaagctta gtgctgctag tttggaatcc                                         30

<210> SEQ ID NO 13
<211> LENGTH: 52
<212> TYPE: DNA
<213> ORGANISM: artificial
<220> FEATURE:
<223> OTHER INFORMATION: primer

<400> SEQUENCE: 13
gcacttaagt ttaggcagtt taacacttct actagaaaaa atgatgaaaa ag                52

<210> SEQ ID NO 14
<211> LENGTH: 52
<212> TYPE: DNA
<213> ORGANISM: artificial
<220> FEATURE:
<223> OTHER INFORMATION: primer

<400> SEQUENCE: 14 cttttttcatc attttttcta gtagaagtgt taaactgcct aaacttaagt gc               52
```

```
<210> SEQ ID NO 15
<211> LENGTH: 46
<212> TYPE: DNA
<213> ORGANISM: artificial
<220> FEATURE:
<223> OTHER INFORMATION: primer

<400> SEQUENCE: 15
atcagtatga ttcagagaag gacattatat gaatgtctta caatgg            46

<210> SEQ ID NO 16
<211> LENGTH: 46
<212> TYPE: DNA
<213> ORGANISM: artificial
<220> FEATURE:
<223> OTHER INFORMATION: primer

<400> SEQUENCE: 16
ccattgtaag acattcatat aatgtccttc tctgaatcat actgat            46
```

NEUROTENSIN-INDUCED TUMOR FORMATION IS REGULATED BY MICRO RNA 133A-AFTIPHILIN-DEPENDENT RECEPTOR RECYCLING

CROSS REFERENCE TO RELATED APPLICATIONS

The present application is a divisional of application Ser. No. 14/891,961, filed Nov. 17, 2015, which application claims priority to U.S. Provisional Application No. 61/824,603, filed May 17, 2013, each of which is incorporated by reference herein in its entirety for all purposes.

GOVERNMENT RIGHTS

This invention was made with Government support of Grant No. DK060729, awarded by the National Institutes of Health. The Government has certain rights in the invention.

REFERENCE TO A SEQUENCE LISTING SUBMITTED VIA EFS-WEB

The content of the ASCII text filee of the sequence listing named "UCLA235USD1_SL", which is 27 kb in size, was created on Sep. 29, 2016, and electronically submitted via EFS-Web herewith the application. The sequence listing is incorporated herein by reference in its entirety.

FIELD OF THE INVENTION

Colorectal cancer (CRC) is one of the most common cancers in the developed world with an overall incidence of 5% in the general population. The 5-year survival rate ranges from 40-60%, although surgical intervention can cure up to 90% of patients if the disease is detected at the early stage. Currently, fecal occult blood test (FOBT), sigmoidoscopy, colonoscopy and double contrast barium enema (DCBE) are used for CRC screening, but in some cases, small polyps may be missed. Therefore, intense research efforts are focusing in the development of novel biomarkers for detection of the disease. Moreover, the identified biomarkers may by themselves represent a pharmaceutical target of CRC.

BACKGROUND OF THE INVENTION

This application presents novel methods of detection, diagnosis, prognosis, prevention, and treatment of inflammatory bowel disease (IBD) and cancers, specifically colorectal cancers (CRCs).

IBD, inclusive of ulcerative colitis (UC) and Crohn's disease (CD), is a chronic inflammatory disease of the gastrointestinal (GI) tract. At present, monoclonal antibodies against TNF-α remains one of the most effective treatments against IBD, in addition, aminosalicylates, corticosteroids and immunosuppressants are also used. However, due to the multi factorial nature of the disease, flare-ups of the disease and side effects associated with the different treatment approaches, in particular corticosteroids are common. Although both genetic and environmental factors contribute to IBD pathogenesis, epigenetic regulators, such as microRNAs may also play an important role in IBD.

CRC is cancer that starts in either the colon or the rectum. Although early intervention by surgery can cure up to 90% patients, CRC is often diagnosed at an advance stage. Colonoscopy remains one of the most sensitive CRC screening tests currently available. Genetic testing of stool DNA is under examination for the feasibility as screening tools. On the other hand, depending on the stages, CRC can be treated by either surgery alone or in combination with chemotherapy. Novel therapeutic modalities are still actively sought. Research by others has shown that AFTPH consists of binding sites with other proteins involved in endocytosis and is crucial to intracellular transport. Our evidence both in vitro (human cancer cell lines) and in vivo (mouse xenograph model) shows that reducing AFTPH levels promotes tumor growth. In addition, we have also shown that AFTPH levels decrease in colon cancer tissue samples when compared to colonic biopsies from normal subjects. Thus. AFTPH represents a novel candidate for CRC screening and a novel therapeutic target for CRC.

G protein-coupled receptor (GPCR) recycling allows cell resensitization to ligand stimulation and sustains signaling. Although microRNAs regulate many physiological functions, their involvement in GPCR recycling is unknown. We have reported that the neuropeptide neurotensin is involved in the pathophysiology of colon cancer and intestinal inflammation. We also showed that recycling of the GPCR neurotensin receptor 1 (NTR1) regulates proliferative and pro-inflammatory responses in colonocytes. Here, we show that in human colonocytes, NT increases miR-133α expression that enhances NTR1 recycling, but not endocytosis, through direct down-regulation of aftiphilin (AFTPH), a protein associated with trafficking. NTR1 induced miR-133α expression by reducing binding of Zinc finger E-box binding homeobox 1 (ZEB1) to the miR-133α promoter, MiR-133α-regulated NTR1 recycling was linked to NT-associated tumor formation. Increased miR-133α and decreased AFTPH mRNA expression was found in human colon cancers, while miR133α and AFTPH mRNA levels were correlated with tumor stage, Thus, we demonstrate a novel mechanism of a GPCR recycling through microRNA expression that may provide a new target for therapeutic approaches in colon cancer.

Neurotensin (NT) is a 13-amino add neuropeptide expressed in the central nervous system and the intestine (Polak, J. M., et al., 1977. Specific localisation of neurotensin to the N cell in human intestine by radioimmunoassay and immunocytochemistry. *Nature* 270:183-184; Castagliuolo, I., et al., 1999. Neurotensin is a proinflammatory neuropeptide in colonic inflammation. *J Clin Invest* 103:843-849). Its high affinity G protein-coupled receptor (GPCR) neurotensin receptor 1 (NTR1) (Tanaka, K.; et at., 1990. Structure and functional expression of the cloned rat neurotensin receptor. *Neuron* 4:847-854) is overexpressed in colon cancer cell lines (Bakirtzi, K., et 2011. Neurotensin Signaling Activates MicroRNAs-21 and -155 and Akt, Promotes Tumor Growth in Mice, and Is Increased in Human Colon Tumors. *Gastroenterology* 141:1749-1761.e1741) and intestinal tumors (Gui, X., et al., 2008. Increased neurotensin receptor-1 expression during progression of colonic adenocarcinoma. *Peptides* 29:1609-1615).

In the intestine, NTR1 signaling promotes both proliferation and inflammation through MAP kinase and NF-κB pathways (Castagliuolo, I., Wang, C. C., Valenick, L., Pasha, A., Nikulasson, S., Carraway, R. E., and Pothoulakis. C. 1999. Neurotensin is a proinflammatory neuropeptide in colonic inflammation. *J Clin invest* 103:843-849; Zhao, D., et al., 2004. Metalloproteinase-dependent transforming growth factor-alpha release mediates neurotensin-stimulated MAP kinase activation in human colonic epithelial cells. *J Biol Chem* 279:43547-43554; Zhao, D., et al., 2007. Neurotensin stimulates expression of early growth response gene-1 and EGF receptor through MAP kinase activation in human colonic epithelial cells. *Int J Cancer* 120:1652-1656; Zhao, D., et al., 2001. Signal transduction pathways mediating neurotensin-stimulated interleukin-8 expression in human colonocytes. *J Biol Chem* 276:44464-44471). NTR1 activation induces differential expression of 38 microRNAs in human colonocytes overexpressing NTR1 (NCM460-NTR1) (Bakirtzi, K.; et al., 2011. Neurotensin Signaling Activates MicroRNAs-21 and -155 and Akt, Promotes Tumor Growth in Mice, and is increased in Human Colon Tumors. *Gastroenterology* 141:1749-1761.e1741).

MicroRNAs are short (19-25 nucleotides); single-stranded RNA molecules, acting as negative transcriptional or post-transcriptional regulators. They bind to the 3' untranslated regions (UTRs) of transcripts (McKenna, et al., 2010. MicroRNAs control intestinal epithelial differentiation; architecture; and barrier function. *Gastroenterology* 139:1654-1664; 1664 e1651) and lead to messenger RNA (mRNA) degradation, or inhibition of translation into protein (Bartel, D. P. 2009. MicroRNAs: target recognition and regulatory functions. *Cell* 136:215-233). MicroRNAs regulate many physiological functions, including inflammation (Contreras. J., et al., 2012. MicroRNAs in inflammation and immune responses, *Leukemia* 26:404-413), metabolism (Rottiers, V., et al., 2012. MicroRNAs in metabolism and metabolic disorders. *Nat Rev Mol Cell Biol* 13:239-250) and cancer development (Croce, C. M. 2009. Causes and consequences of microRNA dysregulation in cancer, *Nat Rev Genet* 10:704-714), including colon cancer (Schetter, A. J., et al., 2011. Alterations of microRNAs contribute to colon carcinogenesis. *Semin Oncol* 38:734-742).

NTR1 is a "class B" receptor with sustained and high affinity binding to β-arrestins, which control receptor desensitization and endocytosis (Oakley, R. H., et al., 2000. Differential affinities of visual arrestin, beta arrestin1, and beta arrestin2 for G protein-coupled receptors delineate two major classes of receptors. *J Biol Chem* 275:17201-17210; Oakley, R. H., et al., 2001, Molecular determinants underlying the formation of stable intracellular G protein-coupled receptor-beta-arrestin complexes after receptor endocytosis. *J Biol Chem* 276:19452-19460). The activated NTR1 internalizes with β-arrestins in NCM460-NTR1 cells and recycles from Rab5a$^+$ early endosomes in a endothelin-converting enzyme-1 (ECE-1)-dependent manner (Law. I. K. M., et al, 2012. Neurotensin-induced pro-inflammatory signaling in human colonocytes is regulated by beta-arrestins and endothelin-converting enzyme-dependent endocytosis and re-sensitization of NT receptor 1. *Journal of Biological Chemistry*).

GPCR trafficking regulates signaling since receptor interaction with β-arrestins mediates desensitization and endocytosis, and receptor recycling generally mediates resensitization (Schmidlin, F., et al., 2001. Dynamin and Rab5a-dependent trafficking and signaling of the neurokinin 1 receptor, *J Biol Chem* 276:25427-25437; Roosterman, D., et al., 2007. Endothelin-converting enzyme 1 degrades neuropeptides in endosomes to control receptor recycling. *Proc Natl Aced Sci USA* 104:11838-11843).

When cells are continuously exposed to NT, NTR1 recycling and resensitization are required for sustained signaling (Law, I. K. M., et al., 2012. Neurotensin-induced pro-inflammatory signaling in human colonocytes is regulated by beta-arrestins and endothelin-converting enzyme-dependent endocytosis and re-sensitization of NT receptor 1. *Journal of Biological Chemistry*). Since differential microRNA expression in response to NT in human colonocytes (Bakirtzi, K., et al., 2011. Neurotensin Signaling Activates MicroRNAs-21 and -155 and Akt, Promotes Tumor Growth in Mice, and Is Increased in Human Colon Tumors. *Gastroenterology* 141:1749-1761,e1741) coincides with NTR1 internalization and recycling to the plasma membrane (Law, I. K. M., et al., 2012. Neurotensin-induced pro-inflammatory signaling in human colonocytes is regulated by beta-arrestins and endothelin-converting enzyme-dependent endocytosis and re-sensitization of NT receptor 1. *Journal of Biological Chemistry*), we hypothesized that some of the NT-regulated microRNAs may play a role in these processes.

Our results indicate that NT-induced miR-133α expression regulates NTR1 recycling to the plasma membrane. We show that aftiphilin (AFTPH) is a downstream target of miR-133α that regulates NTR1 recycling as well as colonic tumor growth in vitro and in vivo. This is the first study providing evidence for an important role of microRNAs in regulation of GPCR recycling that is linked to development of colon cancer.

BRIEF SUMMARY OF THE INVENTION

In a first embodiment, this invention comprises a method of treating colorectal cancer in a subject. In certain embodiments, the treatment comprises administering an effective dose of antisense miR-133α.

In a second embodiment, this invention comprises a method of treating inflammatory bowel disease in a subject. In certain embodiments the treatment comprises administering an effective dose of antisense miR-133α.

In a third embodiment, this invention comprises a method of diagnosing colorectal cancer in a subject wherein an increased expression of miR-133α is detected, wherein the increased expression of miR-133α compared to a control subject is indicative of the presence of colorectal cancer or the likelihood of the colorectal cancer progressing.

In a fourth embodiment, this invention comprises a method of diagnosing inflammatory bowel disease in a subject wherein an increased expression of miR-133α is detected, wherein the increased expression of miR-133α compared to a control subject is indicative of the presence of inflammatory bowel disease or the likelihood of the inflammatory bowel disease progressing.

In any of the first four embodiments, the antisense miR-133α can be administered intracolonically. In any of the first four embodiments, the antisense miR-133α is expressed by a lentivirus. In specific embodiments, the antisense miR-133α expressing lentivirus is administered intravenously.

In any of the first four embodiments, the antisense miR-133α is a locked nucleic acid based miR-133α. In a specific embodiment, the locked nucleic acid based miR-133α is administered intracolonically.

In any of the above described embodiments, the colorectal cancer is a cancer selected from a group comprising carcinomas, adenomatous polyps, adenocarcinomas, colonic carcinoids, colonic polyps, colorectal callous ademomas, colon cancer, bowel cancer, rectal cancer, carcinoid tumors, gastrointestinal stroma tumors, and lymphomas.

In any of the above described embodiments, the irritable bowel syndrome disease is selected from a group comprising Crohn's disease, ulcerative colitis, colitis, collagenous colitis, lymphocytic colitis, ischaemic colitis, diversion colitis. Behcet's disease, and indeterminate colitis.

In a fifth embodiment, this invention comprises a method of treating colorectal cancer in a subject. In certain embodiments the treatment comprises administering an effective dose of a AFTPH polypeptide.

In a sixth embodiment, this invention comprises a method of treating inflammatory bowel disease in a subject. In certain embodiments the treatment comprises administering an effective dose of a AFTPH polypeptide.

In a seventh embodiment, this invention comprises a method of diagnosing colorectal cancer in a subject wherein a decreased expression of AFTPH is detected, wherein the decreased expression of AFTPH compared to a control subject is indicative of the presence of colorectal cancer or the likelihood of the colorectal cancer progressing.

In an eighth embodiment, this invention comprises a method of diagnosing inflammatory bowel disease in a subject wherein a decreased expression of AFTPH is detected, wherein the decreased expression of AFTPH compared to a control subject is indicative of the presence of inflammatory bowel disease or the likelihood of the inflammatory bowel disease progressing.

In specific embodiments, the AFTPH gene is expressed by a lentivirus. In specific embodiments the AFTPH polypeptide is administered intracolonically. In specific embodiments, the lentivirus expressing the AFTPH gene is administered intravenously. In specific embodiments the lentivirus expressing AFTPH gene is administered intravenously. In specific embodiments, the AFTPH polypeptide is a modified AFTPH polypeptide. In specific embodiments, the modified AFTPH polypeptide is administered by direct administration to a tumor. In specific embodiments, the modified AFTPH polypeptide is administered intravenously. In specific embodiments, the modified AFTPH polypeptide is administered intraperitoneally.

In any of the above described embodiments, the colorectal cancer is a cancer selected from a group comprising carcinomas, adenomatous polyps, adenocarcinomas, colonic carcinoids, colonic polyps, colorectal callous ademomas, colon cancer, bowel cancer, rectal cancer, carcinoid tumors, gastrointestinal stromal tumors, and lymphomas.

In any of the above described embodiments, the irritable bowel syndrome disease is selected from a group comprising Crohn's disease, ulcerative colitis, colitis, collagenous colitis, lymphocytic colitis, ischaemic colitis, diversion colitis, Behcet's disease, and indeterminate colitis.

In any of the above described embodiments, the subject is a mammal. In any of the above described embodiments, the subject is a human.

BRIEF DESCRIPTION OF THE DRAWINGS

FIG. 1A shows NTR1 localization in NCM460-NTR1 cells transfected with control or antisense miR-133α. Cells were incubated with vehicle or NT (100 nM) for 1 h, washed and recovered in NT-free medium for 3h or 6h. (arrows, intracellular NTR1; arrowheads, membrane-associated NTR1). Scale, 10 μm. FIG. 1B shows that Mean Fluorescence Intensity (MFI) was measured in the intracellular and cell surface associated NTR1 labeling and the surface and intracellular values were expressed as a ratio (upper panels) and percentage of membrane-associated NTR1 vs total cellular receptor was calculated in each treatment group (lower panel). *P<0.05 when compared to vehicle control group and #P<0.05 when compared to antisense control treatment.

FIG. 2A shows NTR1 localization in NCM460-NTR1 cells transfected with control or antisense miRNA against miR-140, miR-21, miR-210, miR-155, miR-23α, miR-23 beta (β) and miR-331-5p in vehicle control, 100 nM NT treatment for 1 h, 3 h and 6 h after recovery in NT-free medium. (arrows, intracellular NTR1; arrowheads, membrane-associated NTR1) Scale, 10 μm. FIG. 2B shows the percentage of membrane-associated NTR1 vs total cellular receptors in different treatments. *P<0.05.

FIG. 3A shows an IL-8 ELISA on conditioned media from NCM460-NTR1 cells transfected with control mRNA precursors or miR-133α precursors 6 h after vehicle or 100 nM NT treatment. FIG. 3B shows Western blot analysis of ERK1/2 and NF-KB phosphorylation in NCM460-NTR1 cells transfected with control mRNA precursors or miR-133α precursors 2 days prior to 100 nM NT treatment for 5 min and 1 h respectively. *P<0.05 when compared to vehicle control treatment, #P<0.05 when compared to vehicle control treatment in miR-133α-overexpressed group.

FIG. 4A is a diagram showing the complementary binding site of miR-133α (SEQ ID NO: 10) in AFTPH 3' UTR (SEQ ID NO. 9) in different species (Human SEQ ID NO: 1; Chimpanzee SEQ ID NO: 2; Mouse SEQ ID NO: 3; Dog SEQ ID NO: 4; Cat SEQ ID NO: 5; Cow SEQ ID NO: 6; Armadillo SEQ ID NO: 7; Chicken SEQ ID NO: 8). FIG. 4B shows the qPCR analysis of AFTPH levels in NCM460-NTR1 cells transfected with control and antisense miR-133α 2 days prior to NT treatment (100nM) for 30min. FIG. 4C shows a luciferase activity assay of NCM460-NTR1 cells with the above mentioned treatment and exposed to 100 nM NT for 1 h. FIG. 4D shows a luciferase activity assay of cells transfected with plasmids of AFTPH 3' UTR with or without miR-133α binding site 2 days prior to NT (100nM) treatment for 1 h. FIG. 4E shows a luciferase activity assay of HEK293 cells transfected with control or miR-133α precursors 2 days in prior. *P<0.05 when compared to vehicle treatment or control group.

FIG. 5A shows the localization of AFTPH and TGN38 in untreated NCM460-NTR1 cells. FIG. 5B shows the localization of NTR1 and AFTPH in untreated NCM460-NTR1 cells. FIG. 5C shows the localization of NTR1 in NCM460-NTR1 cells transfected with control si-RNAs and siRNAs against AFTPH, and FIG. 5D shows 10 nM Brefeldin A-treatment, followed by treatment with vehicle control, 100 nM NT treatment, 3 h and 6 h in NT-free medium after NT treatment. Arrows, intracellular NTR1; arrowheads, membrane-associated NTR1. Scale, 10 μm (10 micrometers).

FIG. 6A shows Mean Fluorescence Intensity (MFI) of membrane-associated NTR1 in NCM460-NTR1 cells transfected with control siRNAs or si-RNAs against AFTPH 2 days prior to treatment. FIG. 6B shows percentage of membrane-associated NTR1 vs total cellular receptors in NCM460-NTR1 cells were calculated in each treatment. *P<0.05, when compared to vehicle control treatment.

FIG. 7A is a diagram showing the complementary ZEB1 binding site in miR-133α promoter. FIG. 7B shows the qPCR analysis of miR-133α levels in NCM460-NTR1 cells transfected with control si-RNAs or si-RNAs against ZEB1 2 days prior to 100 nM NT exposure for 1 h. FIG. 7C shows a luciferase activity assay of NCM460-NTR1 cells transfected with AFTPH 3' UTR luciferase and control si-RNAs or si-RNAs against ZEB1

(FIG. 7D) qPCR analysis of AFTPH levels in cells with the above mentioned treatment. FIG. 7E shows a chromatin-immunoprecipitation assay (ChIP) of ZEB1 binding sites from NCM460-NTR1 cells incubated with vehicle control or 100 nM NT for 1 hr (FIG. 7F) MiR-133α promoter-driven luciferase activity assay of cells transfected with control si-RNAs and si-RNAs against ZEB1 2 days prior to 100 nM NT exposure for 1 h. FIG. 7G shows a luciferase activity assay of NCM460-NTR1 cells transfected with miR-133α promoter with or without ZEB1 binding site 2 days prior to 100 nM NT treatment, 1 h. *P<0.05 when compared to vehicle treatment in control group.

FIG. 8A shows tumor volume measured from mice xenografts induced by injection of HCT-116 and SW480 cells and treated with vehicle control or NT and antisense miRNA control (as-miR-control) or antisense miR-133α (as-miR-133α) at day 10, 15, 20, 25 and 30. FIG. 8B shows qPCR analysis of miR-133α, AFTPH and IL-8 mRNA levels in tumors from the above mentioned treatment. FIG. 8C shows anchorage-independent colony formation of HCT-116 and SW480 cells transfected with control siRNAs (Si-control) and siRNAs against AFTPH (si-AFTPH). FIG. 8D shows tumor invasion assay of HCT-116 and SW480 of the above mentioned treatment. FIG. 8E shows tumor volume measured from mice xenografts induced by injection of HCT-116 and SW480 cells and treated with control siRNAs (si-control) and siRNAs against AFTPH (si-AFTPH) at day 10, 15, 20, 25 and 30. *P<0.05 when compared to untreated cells or mice.

FIG. 9A shows tumor volume measured from mice xenograft induced by injection of HCT-116 and SW480 cells and treated with vehicle control or miR-133α precusor and antisense miRNA control or antisense miR-133α at day 10, 15, 20, 25 and 30. FIG. 9B shows qPCR analysis of AFTPH mRNA levels in tumors from the above mentioned treatment. *P<0.05 when compared to untreated mice.

FIG. 10A shows qPCR analysis of miR-133α levels in human control (n=5) and colon cancer (n=43) tissues. FIG. 10B shows qPCR analysis of AFTPH levels in the same control and colon cancer tissues. FIG. 10C shows linear regression of AFTPH levels and miR-133α levels in human tumor tissues. FIG. 10D shows qPCR analysis of miR-133α levels in human colon cancer tissues from stage I (n=6), II (n=18), III (n=14) and IV (n=5). FIG. 10E shows qPCR analysis of AFTPH levels in human colon cancer tissues from stage I to IV.

FIG. 13A-B shows that miR-133α and AFTPH levels are differentially regulated in UC patients. FIG. 13A shows qPCR analysis of miR-133α leveis were increased in UC patients (n=12) when compared to normal subjects (n=9). FIG. 13B shows qPCR analysis of AFTPH levels were decreased in UC patients when compared to normal control in the same group of samples (*P<0.05, **P<0.01).

FIG. 14 shows that an overexpression of miR-133α increases pro-inflammatory cytokine expression in vitro. We have previously shown that miR-133α is expressed in human colonocyte cell line NCM460. Here we show the role of miR-133α in pro-inflammatory signaling in vitro. Overexpression of miR-133α in human colonocytes increased IL-8 secretion by ~3 fold (P=0.0001).

FIG. 17A-D shows that antisense miR-133α attenuated the development of TNBS-induced colitis. We have further examined the effect of miR-133α knock-down in experimental colitis. Two doses of antisense miR-133α were administered to C57BL/6J mice via intracolonic route at 24 h and 48 h prior to TNBS-experimental colitis induction as stated above. Colonic tissues were collected 2 days after experimental colitis induction. FIG. 17A shows qPCR analysis of miR-133α levels were reduced in antisense miR-133α-treated mice when compared to mice received control antisense miR (as-miR-control). FIG. 17B shows the representative histological images of colon tissues from mice with the treatments stated above. FIG. 17C shows the scores from histological examination of the colon tissues from mice treated as stated above. There was significant improvement in mucosal integrity and neutrophil infiltration. When compared to control group, antisense miR-133α-treated mice had a significantly lower total histological score (*P<0.05, P<0.01, *P<0.005). FIG. 17D shows a reduced production of proinflammatory cytokines such as lipocalin 2 (lcn2), TNF-α and cxcl1.

DETAILED DESCRIPTION OF THE INVENTION

Overview

Figure 1:
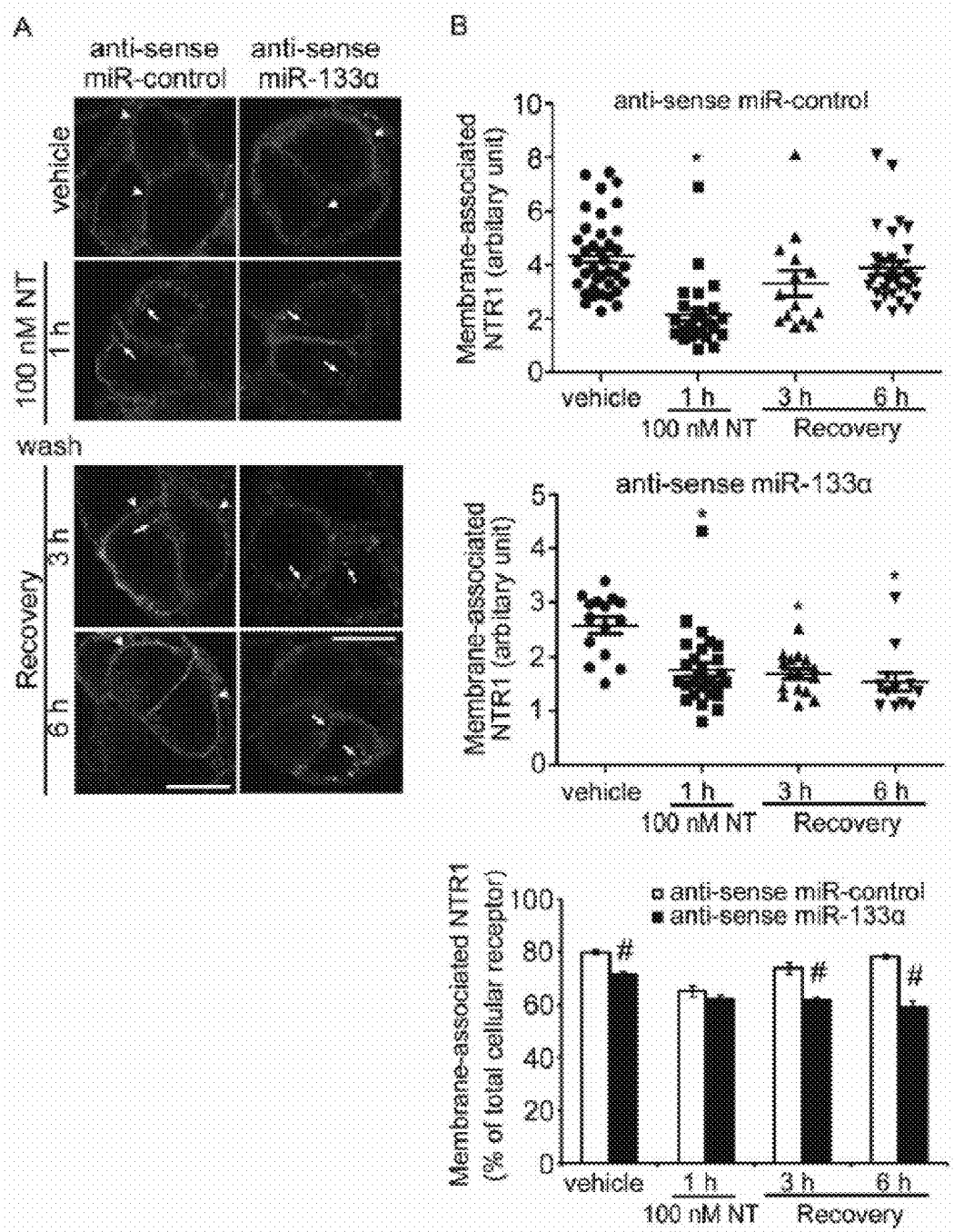
FIG. 1A-B shows that MiR-133α downregulation inhibits receptor recycling.

This is the first report of miR-133α upregulation in colon cancer progression in humans that can also predict CRC stage. This is also the first report showing that miR-133α induces NFκB p65 phosphorylation in human colonocytes. Accordingly, in certain embodiments, miR-133α knockdown treatment can be used to reduce tumor growth in vitro and in vivo.

As described herein, certain embodiments of this application disclose that increased microRNA-133α levels in biopsy samples from colorectal cancer of all tumor stages, including early stage. In certain embodiments, this application discloses that increased miR-133α expression levels are correlated with the severity of tumor development in human colon cancers. In certain embodiments, intratumoral reduction of miR-133α also reduced tumor growth in a mouse xenograft model. Accordingly, as described herein, miR-133α can be used as a CRC screening biomarker and a pharmaceutical target for therapy of CRC.

In certain embodiments, antisense miR-133α treatment can be used to attenuate tumor colony formation in human cancer cells. In specific embodiments, antisense miR-133α treatment can be used to attenuate tumor colony formation in human CRC. In specific embodiments, antisense miR-133α treatment can be used to attenuate tumor colony formation in human cancer cell lines HCT-116 and SW480.

In certain embodiments, antisense miR-133α treatment can be used to reduce cell invasiveness in human cancer cells. In certain embodiments, antisense miR-133α treatment can be used to reduce cell invasiveness in human CRC. In certain embodiments, antisense miR-133α treatment can be used to reduce cell invasiveness in human cancer cell lines HCT-116 and SW480.

In specific embodiments, 50 nM, or 60 nM, or 70 nM, or 80 nM, or 90 nM; or 100 nM, or 120 nM, or 140 nM, or 160 nM, or 180 nM, or 200 nM, or any combination thereof, miR-133α treatment can be used to reduce human colonic adenocarcinoma. In specific embodiments, 50 nM, or 60 nM, or 70 nM, or 80 nM, or 90 nM, or 100 nM, or 120 nM, or 140 nM, or 160 nM, or 180 nM, or 200 nM, or any combination thereof, miR-133α treatment can be used to prevent cell invasion of human colonic adenocarcinoma cells. In specific embodiments, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, or 50 mg/kg, or 60 mg/kg, or 70 mg/ka, or 80 mg/kg, or 90 mg/kg, or 100 mg/kg or any combination thereof, miR-133α treatment can be used to suppress CRC tumor growth in vivo and in vitro when administered intratumorally. In specific embodiments 20 mg/kg miR-133α treatment can be used to suppress CRC tumor growth in vivo and in vitro when administered intratumorally. In specific embodiments 30 mg/kg miR-133α treatment can be used to suppress CRC tumor growth in vivo and in vitro when administered intratumorally. In specific embodiments 40 mg/kg miR-133α treatment can be used to suppress CRC tumor growth in vivo and in vitro when administered intratumorally. In specific embodiments 50 mg/kg miR-133α treatment can be used to suppress CRC tumor growth in vivo and in vitro when administered intratumorally.

In certain embodiments, antisense miR-133α treatment can be administered intratumorally to mediate its tumor suppressing effect. In certain embodiments, antisense miR-133α treatment can be administered intratumorally, intracolonically, intravenously, subcutaneously, orally, or topically. In certain embodiments, the antisense miR-133α treatment can be used to suppress or stop tumor growth, to kill or destroy tumor cells, to prevent tumor growth, or to suppress or prevent tumor metastases. The methods of administration and targeted anti-tumor action are non-limiting examples of antisense miR-133α treatment.

In specific embodiments, the antisense miR-133α treatment is an antisense miR-133α oligonucleotide(s). In a specific embodiment, the oligonucleotide(s) are administered to a patient with CRC intracolonically. In specific embodiments, the antisense miR-133α treatment is an antisense miR-133α expressing lentivirus. In a specific embodiment, the antisense miR-133α expressing lentivirus is administered intravenously. In specific embodiments, the antisense miR-133α treatment is a locked nucleic add-based miR-133α. In a specific embodiment, the locked nucleic acid-based miR-133α is administered to patients with CRC intracolonically.

Furthermore, this is the first report showing increased miR-133α expression in experimental models of colitis or in tissues of patients with inflammatory bowel disease. This is also the first report to show that miR-133α modulates inflammation of any etiology. Thus, it is shown herein that miR-133α is expressed in human colonic epithelial cells and that its overexpression induces increased expression of activated (phosphorylated) NF-κB p65, a known global mediator of inflammation. It is also shown that overexpression of miR-133α in human colonic epithelial cells results in increased expression of the proinflammatory cytokine interleukin-8, one of the most important neutrophil chemoattractans in IBD. It is also shown that intracolonic administration of antisense miR-133α inhibits colonic inflammation (colitis) in a mouse experimental colitis model, as indicated by improved mucosal integrity, lower neutrophil infiltration and total histological score in the colon. It is also shown that increased miR-133α levels in colonic biopsies from patients with ulcerative colitis.

Moreover, there are currently no publications linking miR-133α with inflammation of any etiology, including BD. miR-133α had not been linked to any proinflammatory signaling pathway apart from our own data included in the attached MS (link to the global mediator of inflammation NF-κB) until this disclosure. As described herein, miR-133α is expressed in human colonic epithelial cells and that its overexpression induces increased expression of activated (phosphorylated) NF-KB p65, a known global mediator of inflammation. Furthermore, overexpression of miR-133α in human colonic epithelial cells results in increased expression of the proinflammatory cytokine interleukin-8, one of the most important neutrophil chemoattractans in IBD.

As described herein, certain embodiments of this application disclose that miR-133α levels are increased in colonic biopsies of patients with UC. Overexpression of miR-133α human colonic epithelial cells promoted phosphorylation of the p65 subunit of the global mediator of inflammation NF-κB. In an experimental colitis model, antagonism of miR-133α by antisense miR-133α reduces histologic colitis damage. These evidences suggest that miR-133α may be an important mediator of colitis and possibly inflammation of other organs, a pharmaceutical target for IBD treatment, as well as a biomarker for UC.

In certain embodiments, intracolonic administration of antisense miR-133α inhibits colonic inflammation (colitis), as indicated by improved mucosal integrity, lower neutrophil infiltration and total histological score in the colon. In certain embodiments, ulcerative colitis can be detected by an increased miR-133α levels in colonic biopsies.

Furthermore, it is disclosed herein that Overexpression of miR-133α (100 nM) induces NF-κB p65 phosphorylation and increased IL-8 secretion in human NCM460 colonocytes. Accordingly, in certain embodiments antisense miR-133α treatment can be used to attenuate intestinal inflammation in experimental colitis when administered via the intracolonic route.

In certain embodiments, antisense miR-133α treatment can be administered intracolonically, intravenously, subcutaneously, orally, or topically to treat IBD. In certain embodiments, the antisense miR-133α treatment can be used to suppress or stop IBD or to prevent IBD. The methods of administration and targeted treatment and prevention of IBD are non-limiting examples of antisense miR-133α treatment.

In specific embodiments, the antisense miR-133α oligo can be administered to patients to treat IBD. In specific embodiments, the antisense miR-133α oligo can be administered to patients with IBD intracolonically. In specific embodiments, the antisense miR-133α expressing lentivirus can be administered to patients to treat IBD. In specific embodiments, the antisense miR-133α expressing lentivirus can be administered to patients to treat IBD via intravenous administration. In specific embodiments, locked nucleic acid-based miR-133α (a more stable form) can be administered to patients to treat IBD. In specific embodiments, locked nucleic acid-based miR-133α (a more stable form) can be administered to patients to treat IBD intracolonically. In specific embodiments, levels of miR-133α alone or in combination with other biomarkers can predict UC and/or follow disease progression.

Furthermore, this is the first report showing AFTPH downregulation in human CR This is also the first report showing that AFTPH gene silencing promotes tumor growth in vitro and in vivo. As described for the first time herein, AFTPH gene silencing promotes tumor colony formation in human cancer cell. As described herein for the first time, AFTPH gene silencing promotes cell invasiveness in human cancers.

As described herein, certain embodiments of this application disclose that a reduction in AFTPH levels in biopsy samples is evident in all colorectal cancer tumor stages, and correlated with the severity of tumor development. In certain embodiments, intratumoral reduction of AFTPH also promoted tumor growth in mouse xenograft model. Accordingly, AFTPH can be used as a CRC screening biomarker and pharmaceutical target.

In specific embodiments, this application shows that AFTPH gene silencing promotes human HCT-116 and SW480 colonocyte tumor formation in anchorage-independent growth assay in 15 days. In specific embodiments, this application shows that AFTPH gene silencing promotes human HCT-116 and SW480 cell invasion in invasion assay in 15 days. In specific embodiments, this application shows that AFTPH gene silencing (5 mg/kg) promoted tumor growth in cancer xenograft model with HCT-116 and SW480 colonocytes when administered intratumorally.

In specific embodiments, lentivirus expressing AFTPH may be administered to patients with CRC via intravenous administration. In specific embodiments, AFTPH is negatively regulated by miR-133α, therefore antisense miR-133α treatment may also be used. In specific embodiments, modified AFTPH (functional peptide) administration may be used either directly injected into the tumor or administered intravenously or intraperitoneally.

Definitions

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. In specific embodiments, "treat" or "treating" refers to suppressing colorectal cancer or reducing the invasiveness of colorectal cancer. In specific embodiments, "treating IBD" in a subject comprises reducing intestinal inflammation in a subject.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "therapy," "therapeutic," "treating," "treat," "treatment," "treatment regimen," or "treatment regime" can be used interchangeably and refer broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and reducing or eliminating existing signs and/or symptoms. Therapy includes treating chronic disease ("maintenance") and acute disease. For example, treatment includes treating or preventing relapses or the recurrence of signs and/or symptoms (e.g., inflammation, pain).

Treatments include anti-inflammatory drugs (e.g., sufasalazine, mesalamine, NSAIDs. ImSAIDs, and corticosteroids), immune system suppressors (e.g., azathioprine, mercaptopurine, infliximab, adalimumab, certolizumab pegol, methodtrexate, cyclosporine, and natalizumab), antibiotics (e.g., metronidazol and ciprofloxacin), anti-diarrheals, laxatives, pain relievers, iron supplements, nutritional plan, vitamin B-12 shots, 6-thiopurine therapy, and surgery.

In certain embodiments, the treatment regimen can be modified based on a patient's genotype. Specifically, the treatment regimen can be modified based on whether a patient exhibits an over expression of NTR1 recycling. In other words, the treatment regimen can be modified based on whether a patient exhibits an over expression of miR-133α protein or mRNA and a decreased expression of AFTPH protein or mRNA.

In specific embodiments, "over expression" refers to at least a 1.5 fold increase in expression from a normal or control subject. In specific embodiments, "over expression" refers to at least a 2 fold increase in expression from a normal or control subject. In specific embodiments, "over expression" refers to at least a 2.5 fold increase in expression from a normal or control subject. In specific embodiments, "over expression" refers to at least a 3 fold increase in expression from a normal or control subject. In specific embodiments, "over expression" refers to at least a 4 fold increase in expression from a normal or control subject. In specific embodiments, "over expression" refers to at least a 5 fold increase in expression from a normal or control subject. In specific embodiments, "over expression" refers to at least a 6 fold increase in expression from a normal or control subject. In specific embodiments, "over expression" refers to at least a 7 fold increase in expression from a normal or control subject. In specific embodiments, "over expression" refers to at least a 8 fold increase in expression from a normal or control subject. In specific embodiments, "over expression" refers to at least a 9 fold increase in expression from a normal or control subject. In specific embodiments, "over expression" refers to at least a 10 fold or more increase in expression from a normal or control subject.

As used herein, "diagnosing" refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

As used herein, "predisposition" or "predispose" refers to the increased likelihood or susceptibility of a patient acquiring or developing a disease. For example, it is known in the art that a patient with irritable bowel syndrome is predisposed to eventually developing Crohn's disease. Accordingly, in certain embodiment, expression levels of miR-133α and AFTPH can be measured from, for example, bowel tissue to determine if a patient is predisposed to IBD and/or CRC.

As used herein, "patient" or "subject" refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient." In preferred embodiments, a patient is a human.

As used herein, a "modified" polypeptide refers to a peptide that retains its original function. For example, a polypeptide may be modified by disrupting one or more disulfide bond of the polypeptide while retaining the original polypeptide's function. For example, a polypeptide may be modified by substituting amino acids while retaining the original polypeptide's function. For example, a polypeptide may be modified by coupling one or more additional molecules to the polypeptide while retaining the original polypeptide's function. Specifically, a modified AFTPH polypeptide differs from the non-modified AFTPH but maintains the non-modified AFTPH polypeptide's function. For example, a modified AFTPH polypeptide may be conjugated to one or more molecules or may have amino add substitutions while retaining the non-modified AFTPH polypeptide's fungtion.

The present invention employs oligomeric antisense compounds, particularly oligonucleotides, for use in modulating the function of nucleic acid molecules encoding miR-133α, ultimately modulating the amount of miR-133α produced. This is accomplished by providing antisense compounds which specifically hybridize with one or more nucleic acids encoding miR-133α. As used herein, the terms "target nucleic acid" and "nucleic add encoding miR-133α" encompass DNA encoding miR-133α, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense."

The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of miR-133α. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic adds for antisense. "Targeting" antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding miR-133α. The targeting process also includes determination of a site or sites within this gene for the antisense interaction to occur such that the desired effect, e.g., detection or modulation of expression of the protein, will result.

In certain embodiments, the intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding miR-133α, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In a specific embodiment, the antisense oligonucleotide is the complementary sequence of the target.

In the context of this invention, "hybridizaton" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

The miR-133α inhibitors of the present invention effectively inhibit the activity of the miR-133α RNA/nucleotide or inhibit the expression of the miR-133α RNA/nucleotide. In one embodiment, the activity or expression of miR-133α is inhibited by about 10%. Preferably, the activity or expression of miR-133α is inhibited by about 30%. More preferably, the activity or expression of miR-133α is inhibited by 50% or more. Thus, the oligomeric antisense compounds modulate expression of miR-133α mRNA by at least 10%, by at least 20%, by at least 25%, by at least 30%, by at least 40%, by at least 50%, by at least 80%, by at least 70%, by at least 75%, by at least 80%, by at least 85%, by at least 90%, by at least 95%, by at least 98%, by at least 99%, or by 100%.

It is understood in the art that the sequence of an antisense compound need not be 100% complementary to that of its target nucleic add to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention.

Percent complementarity of an antisense compound with a region of a target nucleic acid can be determined routinely using BLAST programs (basic local alignment search tools). PowerBLAST programs known in the art (Altschul et al., J. Mol. Biol., 1990, 215, 403-410; Zhang and Madden, Genome Res., 1997, 7, 649-656), and targetscan algorithms (available at the Targetscan Organization website).

Percent homology, sequence identity or complementarity, can be determined by, for example, the Gap program (Wisconsin Sequence Analysis Package, Version 8 for Unix, Genetics Computer Group, University Research Park, Madison Ws.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase I and ribonuclease L family of enzymes.

While a suitable form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound.

The antisense compounds of the present invention can be utilized for diagnostic, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. Antisense modulation has, therefore, been harnessed for research use.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

The antisense compounds of the invention are useful for research and diagnostics, because these compounds hybridize to nucleic acids encoding miR-133α. For example, oligonucleotides that are shown to hybridize with such efficiency and under such conditions as disclosed herein as to be effective miR-133α inhibitors are effective primers or probes under conditions favoring gene amplification or detection, respectively. These primers and probes are useful in methods requiring the specific detection of nucleic acid molecules encoding miR-133α and in the amplification of said nucleic acid molecules for detection or for use in further studies of miR-133α.

Hybridization of the antisense oligonucleotides, particularly the primers and probes, of the invention with a nucleic acid encoding miR-133α can be detected by means known in the art. Such means may include conjugation of an enzyme to the oligonucleotide, radiolabelling of the oligonucleotide or any other suitable detection means. Kits using such detection means for detecting the level of miR-133α in a sample may also be prepared.

The specificity and sensitivity of antisense are also harnessed by those of skill in the art for therapeutic uses. Antisense oligonucleotides have been employed as therapeutic moieties in the treatment of disease states in animals and humans. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic add (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 25 nucleotides (i.e. from about 8 to about 25 linked nucleotides). One having ordinary skill in the art will appreciate that this embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in lengt.

Neurotensin-Induced Tumor Formation is Regulated by microRNA-133α-Aftiphilin-Dependent Receptor Recycling Overview. Since microRNAs were first discovered in *C. elegans* (Lee, R. C., et al., 1993. The *C. elegans* heterochronic gene lin-4 encodes small RNAs with antisense complementarity to lin-14. *Cell* 75:843-854), they have been implicated in many physiological roles, including proliferation (Wu, Z. S., et al., 2012. Loss of miR-133α expression associated with poor survival of breast cancer and restoration of miR-133α expression inhibited breast cancer cell growth and invasion. *BMC Cancer* 12:51), differentiation (Chen, X., et al., 2009. In vitro evidence suggests that miR-133α-mediated regulation of uncoupling protein 2 (UCP2) is an indispensable step in myogenic differentiation. *J Biol Chem* 284:5362-5369), apoptosis (Xu, P., et al., 2003. The *Drosophila* microRNA Mir-14 suppresses cell death and is required for normal fat metabolism. *Curr Biol* 13:790-795), stress response (Dresios. J., et al., 2005. Cold stress-induced protein Rbm3 binds 60S ribosomal subunits, alters microRNA levels, and enhances global protein synthesis. *Proc Natl Acad Sci USA* 102:1865-1870) and oncogenesis (Zhao, Y., et al., 2007. Dysregulation of cardiogenesis, cardiac conduction, and cell cycle in mice lacking miRNA-1-2. *Cell* 129:303-317).

Figure 7:
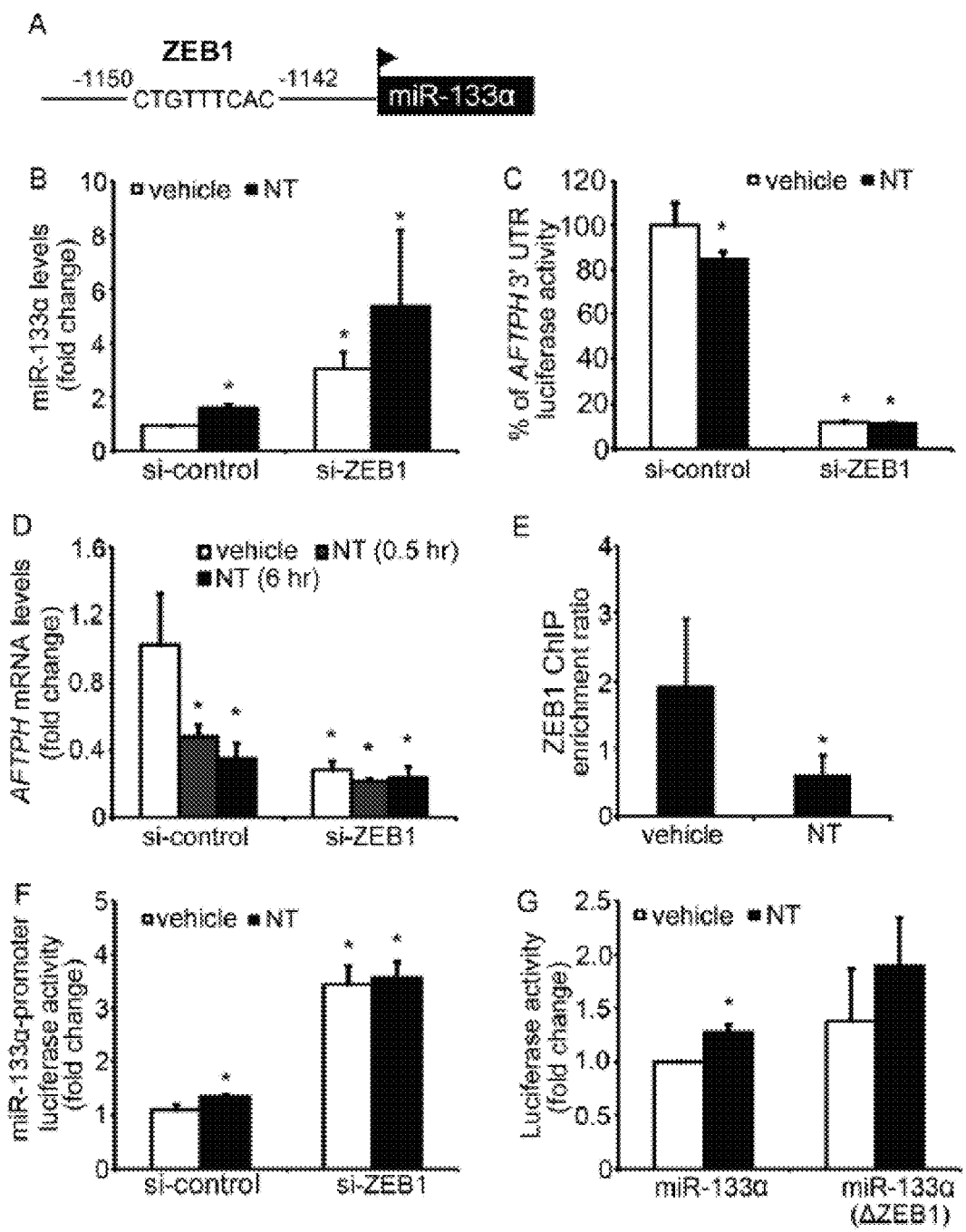
FIG. 7A-G shows that ZEB1 is the negative transcription regulator of miR-133α.

The results presented herein are the first to suggest an important role for microRNAs in GPCR recycling. In the present study, we have correlated NT-induced differential microRNA expression in human colonocytes (Bakirtzi, K., et al., 2011, Neurotensin Signaling Activates MicroRNAs-21 and -155 and Akt, Promotes Tumor Growth in Mice, and Is Increased in Human Colon Tumors. *Gastroenterology* 141:1749-1761.e1741) with the molecular mechanism regulating NTR1 recycling at the transcriptional level. Furthermore, we have also shown that miR-133α and its previously unrecognized downstream target AFTPH are regulated by NT and associated with NT/NTR1-associated tumorigenesis.

miR-133α was first identified as one of the miRNAs involved in muscle development. MyoD and myogenin, two transcription factors associated with muscle differentiation, increase miR-133α expression by binding to its promoter during skeletal muscle differentiation (Chen, X., et al., 2009. In vitro evidence suggests that miR-133α-mediated regulation of uncoupling protein 2 (UCP2) is an indispensable step in myogenic differentiation. *J Biol Chem* 284:5362-5369; Rao, P. K., et al., 2006. Myogenic factors that regulate expression of muscle-specific microRNAs. *Proc Natl Acad Sci USA* 103:8721-8726). In contrast, miR-133α levels are markedly decreased in insulin-like growth factor-induced hypertrophy in cardiac muscle (Hua, Y., et al., 2012. IGF-1 deficiency resists cardiac hypertrophy and myocardial contractile dysfunction: role of microRNA-1 and microRNA-133α. *J Cell Mol Med* 16:83-95). We have identified for the first time ZEB1 as a negative transcription regulator of miR-133α in human colonocytes (FIG. 7).

In mammary epithelial cells ZEB1 activation involves NF-κB activation (Chua, H. L., et al., 2007. NF-kappaB represses E-cadherin expression and enhances epithelial to mesenchymal transition of mammary epithelial cells: potential involvement of ZEB-1 and ZEB-2. *Oncogene* 26:711-724), while NF-κB is an established downstream target of NTR1 colonocyte signaling (Zhao; D., et al., 2001. Signal transduction pathways mediating neurotensin-stimulated interleukin-8 expression in human colonocytes. *J Biol Chem* 276:44464-44471; Zhao, D., et al., 2003. Neurotensin stimulates IL-8 expression in human colonic epithelial cells through Rho GTPase-mediated NF-kappa B pathways. *Am J Physiol Cell Physiol* 284:C1397-1404; Zhao, D., et al., 2005. Neurotensin stimulates interleukin-8 expression through modulation of I kappa B alpha phosphorylation and p65 transcriptional activity: involvement of protein kinase C alpha. *Mol Pharmacol* 67:2025-2031; Zhao, D., et al., 2011. Insulin-like growth factor-1 receptor transactivation modulates the inflammatory and proliferative responses of neurotensin in human colonic epithelial cells. *J Biol Chem* 286:6092-6099). ZEB1 is related to epithelial-mesenchymal transition and histone deacetylase downregulation in pancreatic cancer metastasis (Aigner. K., et al., 2007. The transcription factor ZEB1 (deltaEF1) promotes tumour cell dedifferentiation by repressing master regulators of epithelial polarity. *Oncogene* 26:6979-6988; Peinado, H., et al., 2007. Snail, Zeb and bHLH factors in tumour progression: an alliance against the epithelial phenotype? *Nat Rev Cancer* 7:415-428; Hurt, E. M., et al., 2008, Expression of the ZEB1 (deltaEF1) transcription factor in human: additional insights. *Mol Cell Biochem* 318:89-99; Aghdassi, A., S et al., 2012. Recruitment of histone deacetylases HDAC1 and HDAC2 by the transcriptional repressor ZEB1 downregulates E-cadherin expression in pancreatic cancer. *Gut* 61:439-448).

Our results show that gene silencing of ZEB1 increases miR-133α transcription and downregulates AFTPH, the downstream target of miR-133α (FIG. 7B-D), while NT exposure reduces ZEB1 binding to miR-133α promoter region (FIG. 7E). ZEB1 binding to miR-133α promoter may be crucial to the physiological function of NTR1/miR-133α in cancer cells.

Figure 4:
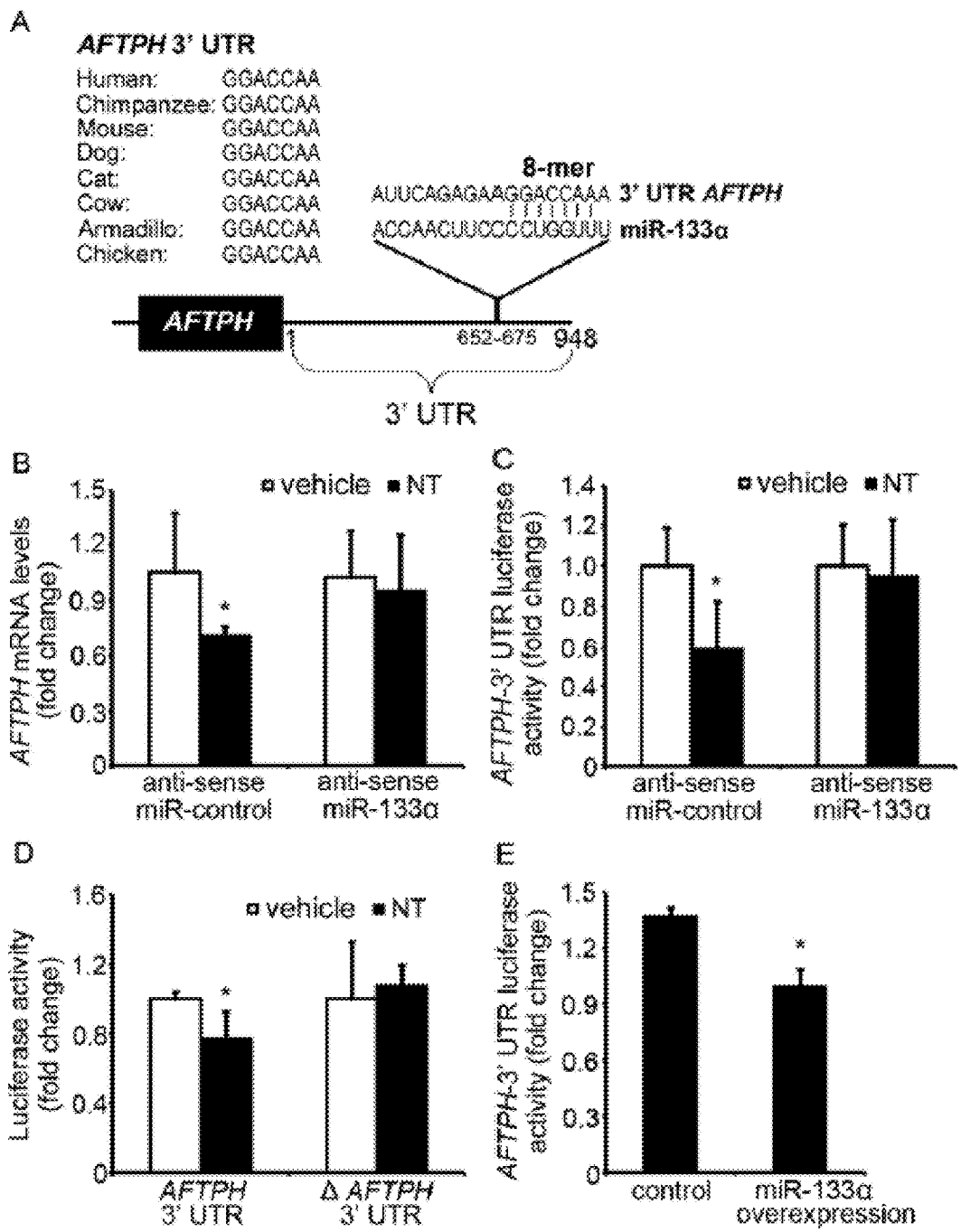
FIG. 4A-E, FIG. 4A-E shows AFTPH is the binding target of miR-133α.

An online data search identified AFTPH as a potential downstream target of miR-133α and cross-species sequence analysis suggested that miR-133α/AFTPH interaction may be highly conserved (FIG. 4A). Our observation that AFTPH transcription in vitro is down-regulated after NT exposure (FIGS. 4B and 4C) or miR-133α overexpression in the absence of NT stimulation (FIG. 4E) supports this notion.

AFTPH binds to proteins involved in trafficking, such as clathrin and adaptor proteins (AP-1, AP-2) (Mattera, R., et al., 2004. Definition of the consensus motif recognized by gamma-adaptin ear domains. J Biol Chem 279:8018-8028) and is localized in the TGN in NCM460-NTR1 cells and neurons (Burman, J. L., et al., 2005. Aftiphilin is a component of the clathrin machinery in neurons. *FEBS Lett* 579: 2177-2184.). Although AFTPH gene silencing does not alter TGN morphology (Hirst, J., et al., 2005. The aftiphilin/p200/gamma-synergin complex. *Mol Biol Cell* 16:2554-2565), it leads to unregulated exocytosis of Weibel-Palade bodies in endothelial cells (Lui-Roberts, et al., 2008. Aftiphilin and gamma-synergin are required for secretagogue sensitivity of Weibel-Palade bodies in endothelial cells. *Mol Biol Cell* 19:5072-5081).

Some GPCRs traffic from early endosomes to the TGN before recycling back to the plasma membrane (Lelouvier, B., et al., 2008. Dynamics of somatostatin type 2A receptor cargoes in living hippocampal neurons. *J Neurosci* 28:4336-4349; Csaba, Z., et al., 2007. Activated somatostatin type 2 receptors traffic in vivo in central neurons from dendrites to the trans Golgi before recycling. *Traffic* 8:820-834; Escola, J. M., et al., 2010, CC chemokine receptor 5 (CCR5) desensitization: cycling receptors accumulate in the trans-Golgi network, *J Biol Chem* 285:41772-41780), depending on receptor phosphorylation sites (Wang, F., et al., 2008. Phosphorylation state of mu-opioid receptor determines the alternative recycling of receptor via Rab4 or Rab11 pathway. *Mol Endocrinol* 22:1881-1892) and duration of stimulation (Toy-Miou-Leong. M., et al., 2004. Receptor trafficking via the perinuclear recycling compartment accompanied by cell division is necessary for permanent neurotensin cell sensitization and leads to chronic mitogen-activated protein kinase activation. *J Biol Chem* 279:12636-12646).

Figure 5:
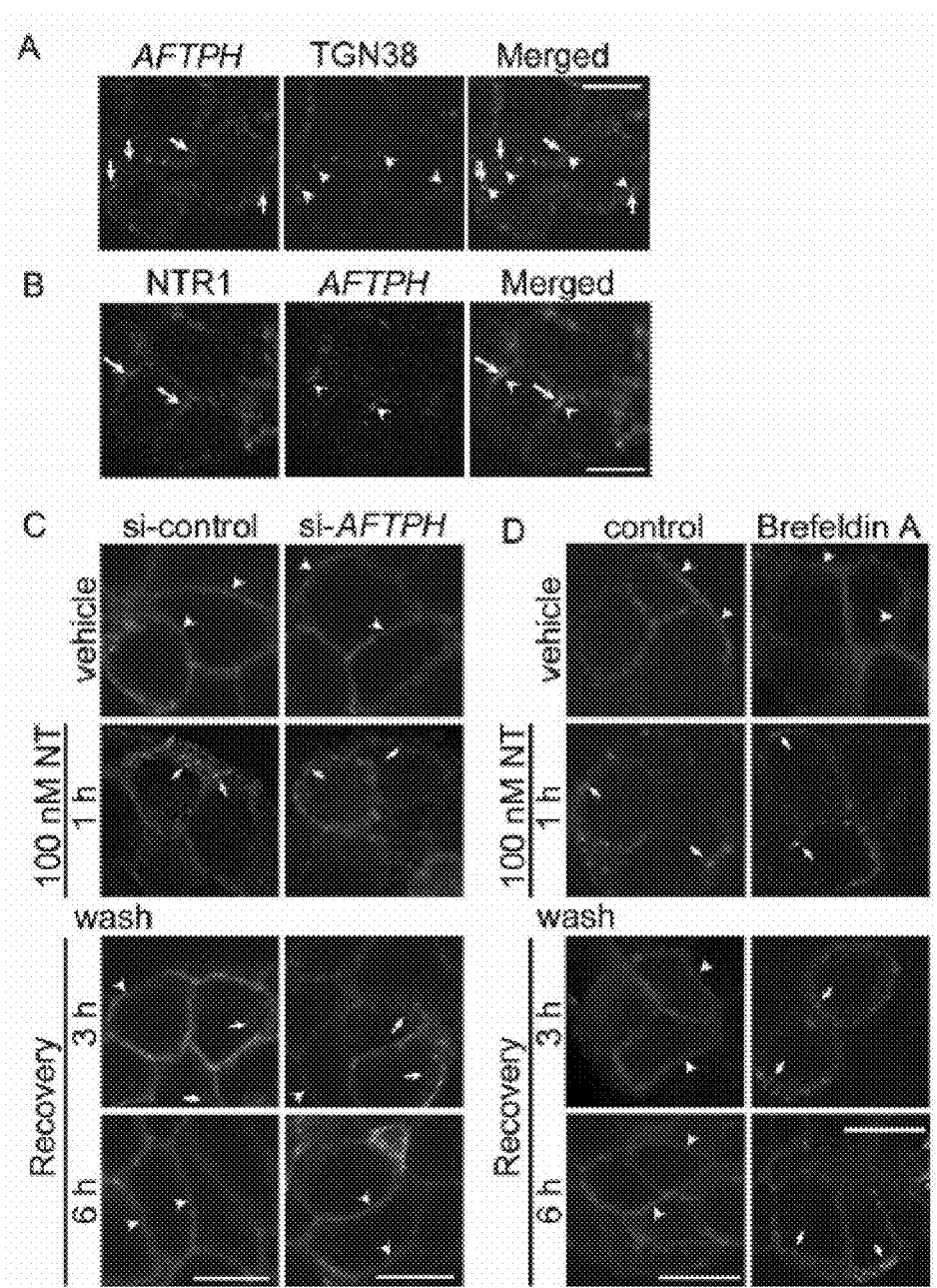
FIG. 5A-D shows that AFTPH regulates NTR1 recycling.

Rapid resensitization of colonocytes to sustained NT exposure is achieved by recycling of NTR1 from Rab5+ early endosomes to the plasma membrane (Law. I. K. M., et al., 2012. Neurotensin-induced pro-inflammatory signaling in human colonocytes is regulated by beta-arrestins and endothelin-converting enzyme-dependent endocytosis and re-sensitization of NT receptor 1. *Journal of Biological Chemistry*), while under chronic stimulation, NTR1 is recycled from the perinuclear recycling compartments to the plasma membrane (Toy-Kiliou-Leong, M., et al., 2004. Receptor trafficking via the perinuclear recycling compartment accompanied by cell division is necessary for permanent neurotensin cell sensitization and leads to chronic mitogen-activated protein kinase activation. *J Biol Chem* 279:12636-12646). In NCM460-NTR1 cells, treatment with Brefeldin A, an inhibitor to trans-Golgi transport, leads to the accumulation of endocytosed NTR1 (FIG. 5D). Based on these considerations our data suggest that TGN-localized AFTPH regulates NTR1 recycling in human colonocytes.

Although miR-133α has been suggested as tumor growth suppressor in bladder, breast, esophageal, and prostate cancer (Wu, Z. S., et al., 2012. Loss of miR-133α expression associated with poor survival of breast cancer and restoration of miR-133α expression inhibited breast cancer cell growth and invasion. *BMC Cancer* 12:51; Kano, M., et al., 2010. miR-145, miR-133α and miR-133b: Tumor-suppressive miRNAs target FSCN1 in esophageal squamous cell carcinoma, *Int J Cancer* 127:2804-2814; Yoshino, H., et al., 2011. The tumour-suppressive function of miR-1 and miR-133α targeting TAGLN2 in bladder cancer. *Br J Cancer* 104:808-818; Kojima, S., et al., 2012. Tumour suppressors miR-1 and miR-133α target the oncogenic function of purine nucleoside phosphorylase (PNP) in prostate cancer. *Br J Cancer* 106:405-413), our results show that miR-133α promotes NT-induced colon tumor colony formation.

Figure 8:
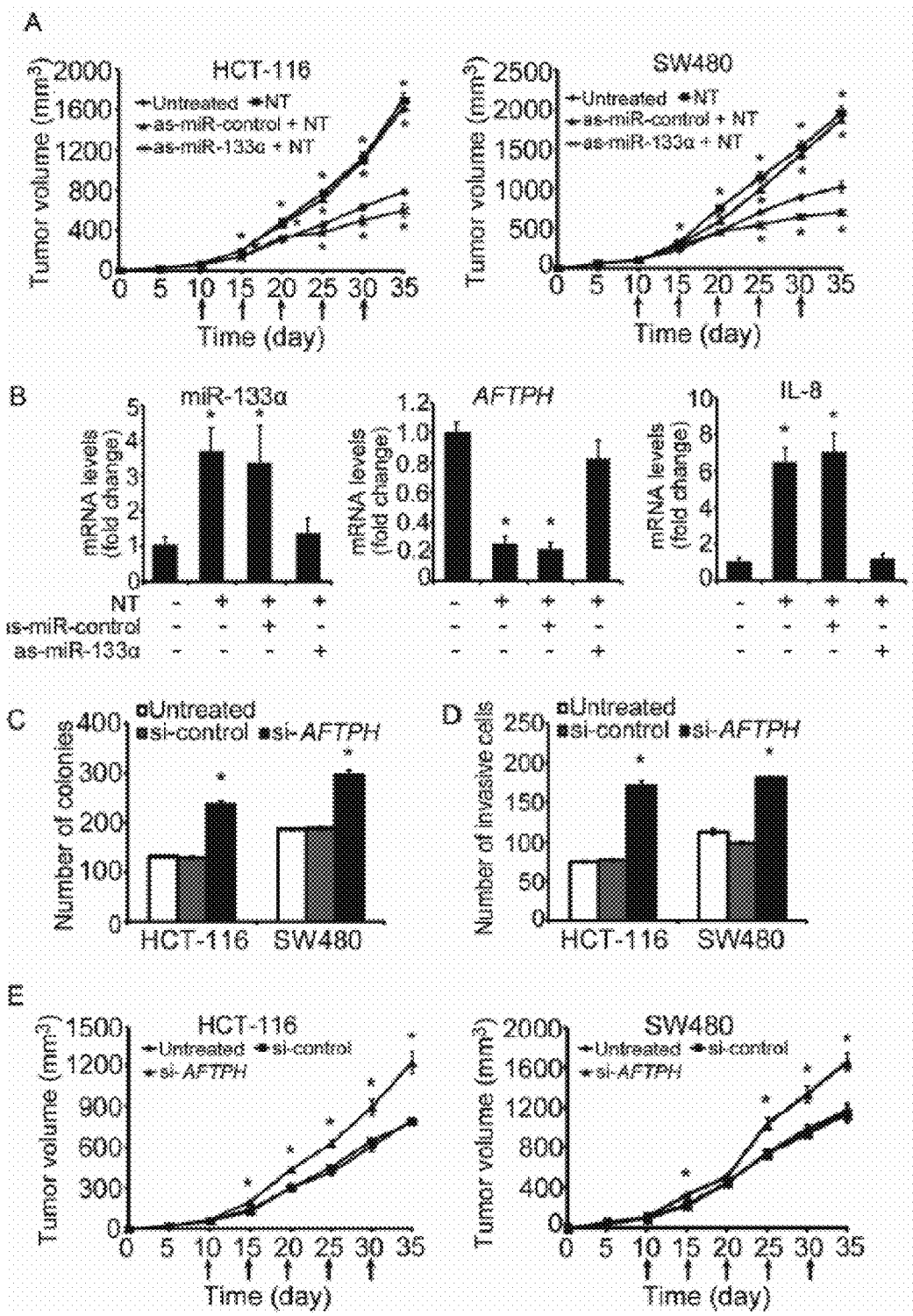
FIG. 8A-E shows that MiR-133α and AFTPH regulate tumor growth in vitro and in vivo.

Inhibition of miR-133α significantly attenuated NT-induced tumor growth in vivo (FIG. 8A). Its downstream target, AFTPH, localized in TGN, promotes tumor colony formation in vitro (FIG. 8C) and in vivo (FIG. 8E) by suppressing NTR1 recycling. Consistent with our findings, inhibition of TGN transport is associated with anti-proliferative effects in vitro (Larsson, D. E., et al., *Anticancer Res* 26:4125-4129; Larsson, D. E., et al., 2009. Combination analyses of anti-cancer drugs on human neuroendocrine tumor cell lines. *Cancer Chemother Pharmacol* 65:5-12; Larsson, D. E., et al., 2010. The cytotoxic agents NSC-95397, brefeldin A, bortezomib and sanguinarine induce apoptosis in neuroendocrine tumors in vitro. *Anticancer Res* 30:149-156; Wallen, E., et al., 2000. Brefeldin A induces p53-independent apoptosis in primary cultures of human prostatic cancer cells. *J Urol* 164:836-841) and in vivo (Sausville, E. A., et al., 1996. Antiproliferative effect in vitro and antitumor activity in vivo of brefeldin A. *Cancer J Sci Am* 2:52-58).

Figure 10:
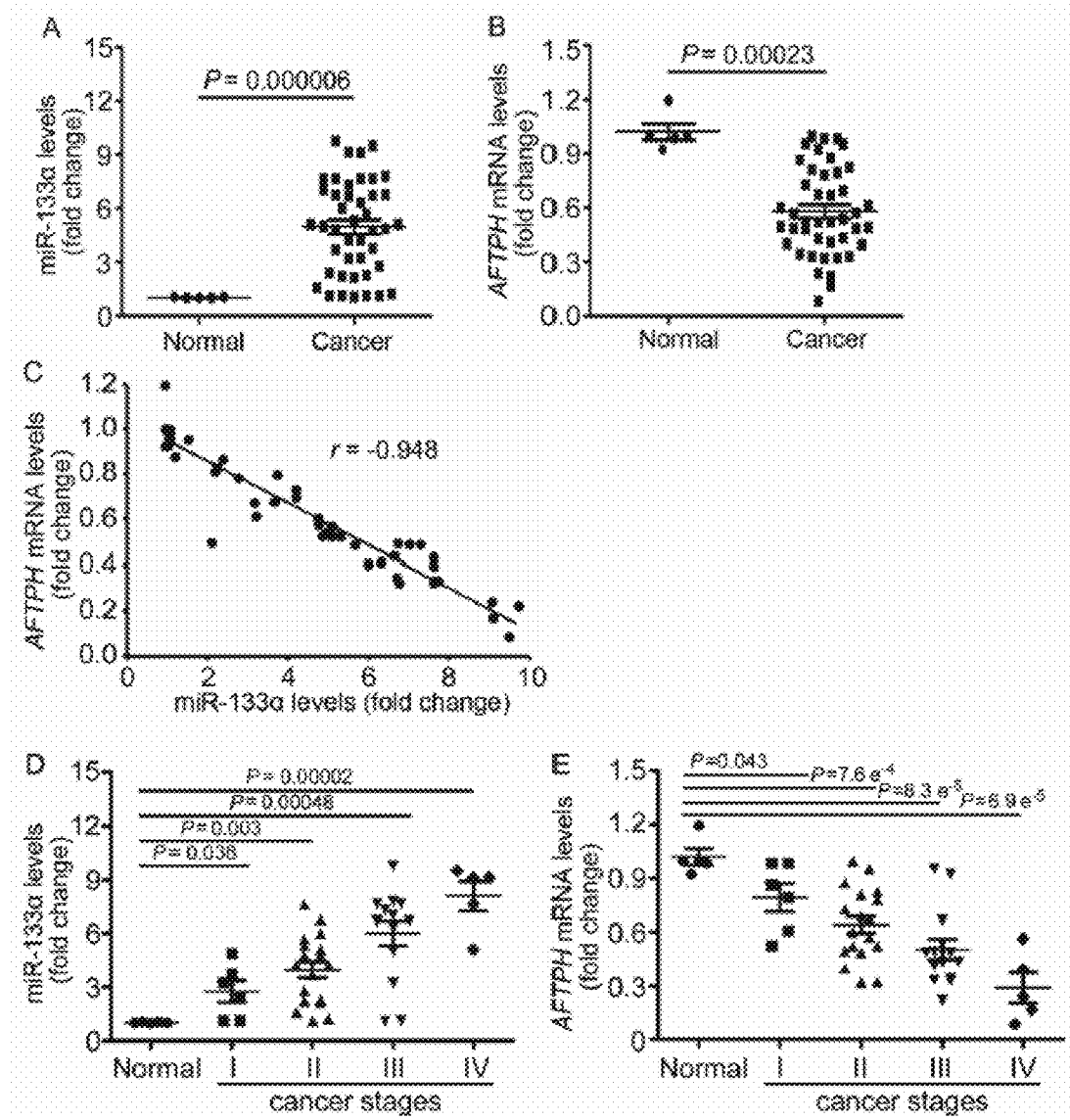
FIG. 10A-E shows that MiR-133α levels correlates with colon cancer progression.

MiR-133α is a potential biomarker for colorectal cancer (Ma, Y., et al., 2012. Candidate microRNA biomarkers in human colorectal cancer: systematic review profiling studies and experimental validation. *Int J Cancer* 130:2077-2087), while HDAC activity is regulated by MAP kinase signaling, at least partially by downregulating NTR1 expression (Wang, X., et al., 2010. Suppression of neurotensin receptor type 1 expression and function by histone deacetylase inhibitors in human colorectal cancers. *Mol Cancer Ther* 9:2389-2398). Moreover, miR-133α transcription increases in colon cancer tissues (FIG. 10A) and with colon tumor progression and metastasis (FIG. 10D) and is inversely proportional to AFTPH levels in human tumor samples (FIG. 10C).

In summary, NT-associated tumor growth is modulated by NTR1 recycling through NT-regulated miR-133α/AFTPH signaling pathway. Interfering with miR-133α/AFTPH-associated NTR1 recycling from TGN to the plasma membrane may represent a novel approach to inhibit colon cancer development.

Cell culture. NCM460-NTR1 cells were generated from normal human colon mucosal epithelial cells, NCM460 cells (INCELL) as previously described (Bakirtzi. K., et al., 2011. Neurotensin Signaling Activates MicroRNAs-21 and -155 and Akt, Promotes Tumor Growth in Mice, and Is Increased in Human Colon Tumors. *Gastroenterology* 141:1749-1761, e1741). HCT-116 and SW480 cells were maintained in McCoy's 5a Medium Modified and Roswell Park Memorial Institute (RPMI) 1640 medium, supplemented with 10% fetal bovine serum respectively.

Immunofluorescence. NCM460-NTR1 cells were transfected with antisense miR-133α (as-miR-133α) (Ambion) and its control using siPORTNeoFX transfection reagent (Applied Biosystems) or siRNA against AFTPH and its control (Santa Cruz) using Lipofectamine™ RNAiMAX (Invitrogen) where appropriate. Cells were serum-fasted overnight 2 d post transfection and exposed to 100 nM NT for 1 h. For NTR1 recovery studies, cells were washed with Phosphate Buffered Saline (PBS) twice and replenished with NT-free medium supplemented with 10 μg/ml Brefeldin A (Santa Cruz) or vehicle (Law, I. K. M., et al., 2012. Neurotensin-induced pro-inflammatory signaling in human colonocytes is regulated by beta-arrestins and endothelin-converting enzyme-dependent endocytosis and re-sensitization of NT receptor 1. *Journal of Biological Chemistry*). Cells were fixed in PBS containing 4% (w/v) paraformeldehyde (pH 7.4, 20 min, 4° C.) and blocked in PBS containing 3% bovine serum and 0.1% Triton X. Cells were incubated (16 h, 4° C.) with the following antibodies (Santa Cruz): goat anti-NTR1 (1:100), goat anti-AFTPH (1:100) and rabbit anti-TGN38 (1:100). Cells were washed and incubated (2 h, room temperature) with bovine anti-goat IgG or bovine-anti-rabbit IgG conjugated to FITC or Texas Red (Santa Cruz, 1:500). After washing with PBS, cells were mounted with UltraCruz (Mounting Medium (Santa Cruz) and imaged with a Leica TCS SP8 laser scanning confocal microscope (North Ryde, NSW, Australia) using a Leica HCX PL APO 63× oil immersion objective (numerical aperture 1.4). Five Z-stack images were captured (1024× 1024 pixel resolution) per treatment.

Image analysis protocol. Substacks of five optical sections were generated per image and were analyzed using Images J with MacBiophotonics plugins. Briefly, a region of interest (ROI) within the cell surface was defined and then enlarged by 1 μm to generate a second ROI. Mean fluorescence intensity was measured for these two regions, representing the intracellular and cell surface associated NTR1 labeling, respectively. The relative surface and intracellular values were expressed as a ratio. Data were presented as either ratios or as a percentage of cell surface NTR1 vs total cellular receptor (mean±SEM). Only cells with a defined nucleus were analyzed and only within cell comparisons were made. Treatment groups were compared by one-way ANOVA with Dunnet's post-hoc test.

Cloning and site-directed mutagenesis. The miR-133α promoter-driven luciferase reporter construct (pGL3-miR-133α) was generated by ligating PCR products encoding the genomic region of 2000 bp upstream to miR-133α was Xho1/HindIII digest and pGL3-Basic (Promega). The primers used are i) miR-133α Xho1 F: ccgctcgagtttcaaagaaatt-agttcaaagcttaa (SEQ ID NO: 11); ii) miR-133α HindIII R: cccaagcttagtgctgctagtttggaatcc (SEQ ID NO: 12). The following site-directed mutagenesis was done using QuikChange II XL site-directed mutagenesis Kit (Agilent Technologies) according to the manufacturer's instructions. ZEB1 binding site on the miR-133α promoter region (pGL3-miR-133α-ΔZEB1) was deleted using with primers: iii) miR133α-del216: gcacttaagtttaggcagtttaacacttctacta-gaaaaaatgatgaaaaag (SEQ ID NO: 13); iv) miR133α-del216antisense: cttttcatcatttttctagtagaagtgttaaactgc-ctaaacttaagtgc (SEQ ID NO: 14). AFTPH 3' UTR luciferase reporter plasmid was purchased from Switchgear Genomics and miR-133α binding site was deleted (AFTPH 3'UTR-ΔmiR-133α) with primers: v) AFTPH-del198: atcagtatgat-tcagagaaggacattatatgaatgtcttacaatgg (SEQ ID NO: 15); vi) AFTPH-98-antisense: ccattgtaagacattcatataatgtccttctctgaat-catactgat (SEQ ID NO: 16).

Luciferase assays. pGL3-miR-133α or pGL3-miR-133α-ΔZEB1 and pRL-TK (Promega, control) were transfected to NCM460-NTR1 cells using lipofectamine 2000 (Invitrogen). For AFTPH 3' UTR-associated luciferase activity; AFTPH 3' UTR luciferase reporter plasmid or AFTPH 3' UTR-ΔmiR-133α luciferase reporter plasmid and R01_3 UTR (Switchgear Genomics, control) were transfected to NCM460-NTR1 cells in the presence of as-miR-133α and its control (Ambion) and in HEK293 cells in the presence of miR-133α precursor and its control (Ambion). Two days after transfection NCM460-NTR1 cells were exposed to NT (1 h), while luciferase activities in transfected HEK293 cells were measured without NT exposure. Firefly and *Renilla* luciferase cell activities were detected using Dual-luciferase reporter assay system (Promega). The relative miR-133α promoter-driven luciferase activities were calculated by normalizing Firefly luciferase activity with that from *Renilla* luciferase. The relative AFTPH 3' UTR-associated luciferase activities were calculated by normalizing AFTPH 3' UTR-associated luciferase activities with R01_3' UTR luciferase activity. Results were presented as the relative luciferase activity (mean±SEM) from at least three independent sets of experiments, each with five replicated measurements.

Immunoblot analysis. NCM460-NTR1 cells were washed with ice-cold PBS after various treatments and incubated with radiolabelled immunoprecipitation assay buffer containing protease inhibitors, phenylmethylsulfonyl fluoride and sodium orthovanadate (Santa Cruz) for 5 min. The insoluble debris was removed by centrifugation at 12000 rpm, 15 min at 4° C. and supernatants were analyzed by immunoblot analysis. Equal amount of cell lysates were loaded (~35 µg) and transferred to nitrocellulose membrane. The membrane was blocked with 5% non-fat dry milk (w/iv) in Tris-buffered saline with 0.1% Tween 20 (TBS-T). Appropriate antibodies were incubated with the membranes overnight at 4° C. washed with TBS-T and incubated with appropriate secondary antibodies conjugated to horseradish peroxidase. Signals from target proteins were detected with SuperSignal chemiluminescent substrate (Pierce). Immunoblot bands were quantified by densitometry using Multi Gauge V3.1 (Fuji).

Messenger RNA and microRNA expression analysis. NCM460-NTR1 cells were washed once with ice-cold PBS after various treatments. Total RNA was extracted by TRIzol (Life technologies) and reverse-transcribed into first strand cDNAs using random decamers and reverse transcriptase (Invitrogen) for mRNA expression analysis. Complementary DNAs for microRNA expression analysis were prepared with mirVana quantitative reverse-transcription PCR miRNA Detection Kit and quantitative reverse-transcription PCR primer sets according to the manufacturer's instructions (Ambion).

IL-8 ELISA. NCM460-NTR1 cells were stimulated with 100 nM NT for 6 h after various treatments. IL-8 in supernatants was measured by Duo-Set® ELISA for IL-8 (R&D Systems) according to the manufacturer's instructions.

Chromatin Immunoprecipitation (ChIP). NCM460-NTR1 cells were cross-linked and fixed after NT exposure for 1 h using Pierce Agarose ChIP kit (Thermo Scientific) according to the manufacturer's instructions. The ZEB1 binding region was Immunoprecipitated by rabbit anti-ZEB1 antibody (Bethyl Laboratories). ZEB1 binding was quantified by real time PCR using a primer complementary to ZEB1 binding site in miR-133α promoter region (Applied Biosystems, assay ID: AJPACV3, Part no. 4441114).

Anchorage-independent growth assays. Anchorage-independent growth assays were performed as described (Bakirtzi, K., et al., 2011, Neurotensin Signaling Activates MicroRNAs-21 and -155 and Akt, Promotes Tumor Growth in Mice, and Is Increased in Human Colon Tumors. *Gastroenterology* 141:1749-1761.e1741). HCT-116 and SW480 cells were transfected with miR-133α or si-AFTPH 2 days prior to the assay. In addition, SW480 cells were treated with 2.5, 5, 10 µg/ml brefeldin A in the presence of 100 nM NT. Triplicates of 5,000 cells were suspended in complete growth media supplemented with 0.4% agarose [mixing 2% agarose with complete growth media in 1:4 (v/v)). Cell mixtures were layered on 0.8% agarose and fed with complete growth media supplemented with 0.4% agarose every 6-7 days. The number of colonies was counted after 15 days. Experiments were repeated 3 times. Statistical significance was calculated using the Student's t-Test.

Xenograft experiments. $6 \times 10^6$ HCT-116 or SW480 cells were injected subcutaneously in the right flank of athymic nude (nu/nu) mice (Charles River Laboratories). When the tumors reached a size of ~100 mm³ (10 days) mice were randomly distributed in different groups (4 mice/group). Effects of miR-133α as a mediator of NT tumorigenic activity, the tumor-injected mice were administered intratumorally as follows: i) untreated, ii) NT 100 nM every 5 days until day 30, iii) 5 mg/kg of as-miR-control and NT (100 nM), iv) 5 mg/kg of as-miR-133α and NT (100 nM). Effects of AFTPH inhibition on tumor growth. The tumor-injected mice were divided in the following groups, i) untreated, ii) 10 mg/kg siRNA-negative control (si-control) and iii) 10 mg/kg siRNA against AFTPH (Si-AFTPH) intratumorally. Effects of miR-133α on tumor growth. Mice from the above treatment were divided into 5 groups and subjected to the following treatments, i) untreated, ii) microRNA negative control (miR-control), iii) miR-133α, iv) antisense-miR-negative control (as-miR-control) and v) antisense-miR-133α (as-miR-133α) intratumorally. The dosage of each treatment was 5 mg/kg and all treatments were performed every 5 days until day 30. In all experiments, tumor growth was monitored every five days for a total period of 35 days and tumor volumes were calculated by the equation $V(mm^3)=axb^2/2$, where a is the largest diameter and b is the perpendicular diameter.

RNA expression studies in patient samples. RNAs were extracted from 5 normal and 43 colon cancer tissues were obtained from OriGene Technologies. MiR-133α levels and mRNA expression of AFTPH were determined by real-time PCR analysis.

Statistical analysis. All in vitro results were derived from at least of three sets of repeated experiments and expressed as means±SD and analyzed with Student's t-Tests. Results from immunofluoresence and in vivo studies were analyzed with one-way-ANOVA (Prism 5). Studies in human tissues were analyzed with Two Sample t-Test (Origin 8.6 software). In all statistical comparisons, P<0.05 was used to indicate significant differences.

miR-133α is a Novel Target for Colitis and Inflammatory Bowel Disease

Overview. Inflammatory bowel disease (IBD) that includes ulcerative colitis (UC) and Crohn's disease (CD), is a chronic inflammatory disease of the gastrointestinal (GI) tract. (Monoclonal antibodies against TNF-α remain one of the most effective treatments against IBD. In addition aminosalicylates, corticosteroids and other immunomodulators/immunosuppressants are also used as treatment modalities. However, remissions are common since IBD is a multifactorial disease, while all above treatment modalities are associated with several and some times debilitating side effects. Although both genetic and environmental factors contribute to IBD pathogenesis, epigenetic regulators; such as microRNAs may also play an important role IBD. MicroRNAs are short (19-25 nucleotides), single-stranded RNA molecules; acting as negative transcriptional regulators. They bind to the 3' untranslated regions (UTRs) of transcripts (McKenna L B, Schug J. Vourekas A, et al. MicroRNAs control intestinal epithelial differentiation; architecture; and barrier function. Gastroenterology 2010.139:1654-64, 1664) and lead to messenger RNA (mRNA) degradation, or inhibition of translation into protein (Bartel D R MicroRNAs: target recognition and regulatory functions. Cell 2009.136:215-33). In support of this invention, we have shown that in experimental colitis model, intracolonic administration of antisense miR-133α reduces intestinal inflammation, while overexpression of this microRNA in human colonic epithelial cells activates the global mediator of inflammation NF-κB and increases expression of the potent IBD-related human chemokine interleukin-8. The above evidences suggest that miR-133α may be an important mediator in IBD and a target for IBD treatment.

Previous studies by others have shown that miR-133α is crucial to cardiomyocyte development and miR-133α may also be a biomarker for other cancer types such as breast (Wu Z S, Wang C Q, Xiang R, et al. Loss of miR-133α expression associated with poor survival of breast cancer and restoration of miR-133α expression inhibited breast cancer cell growth and invasion. BMC Cancer 2012.12:51), bladder (Yoshino H, Chiyomaru T, Enokida H, et al. The tumour-suppressive function of miR-1 and miR-133α targeting TAGLN2 in bladder cancer. Br J Cancer 2011.104: 808-18), esophageal (Kano M, Seki N, Kikkawa N, et al. miR-145, miR-133α and miR-133b: Tumor-suppressive miRNAs target FSCN1 in esophageal squamous cell carcinoma. Int J Cancer 2010.127:2804-14), and colorectal cancer (Ma Y, Zhang P, Yang J, e al. Candidate microRNA biomarkers in human colorectal cancer: systematic review profiling studies and experimental validation. *Int J Cancer* 2012.130:2077-87). However, so far, miR-133α is not related to inflammation of any etiology.

Figure 12:
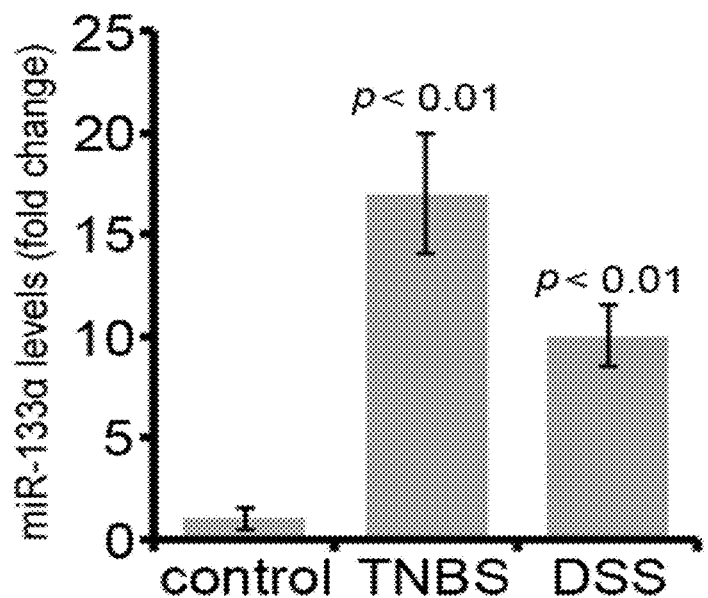
FIG. 12 shows that MiR-133α is upregulated in samples from experimental colitis. miR-133α expression was examined in colon tissues in C57/BL6J mice with experimental colitis. C57/BL6J male mice received intracolonic administration of 2,4,6-TNBS (500 mg/kg) or DSS (5% w/v in drinking water) and colon tissues were collected at day 2 and 5 respectively. Expression of miR-133α was significantly increased in both TNBS- and DSS-induced colitis (P<0.01).
Figure 15:
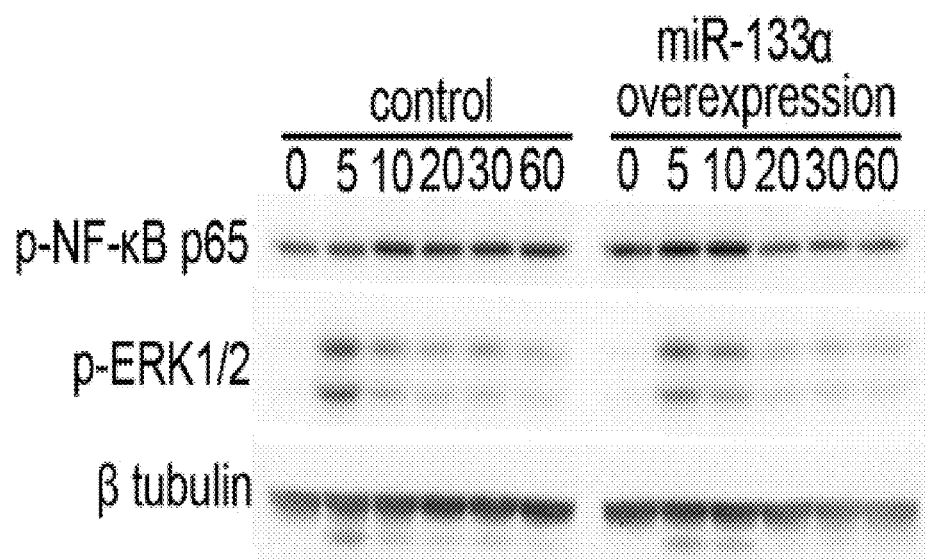
FIG. 15 shows the role of miR-133α in pro-inflammatory signaling. Pro-inflammatory responses were induced by neurotensin (100 nM), a neuropeptide/hormone and a mediator of intestinal inflammation in human colonocytes. Cells lysates were collected at 0, 5, 10, 15, 30 and 60 min after neurotensin exposure. Moreover, overexpression of miR-133α in human colonic epithelial NCM460 cells resulted in a stronger basal and more sustained NF-KB activation. This suggests that miR-133α plays an important role in regulating pro-inflammatory signaling in human colonocytes.
Figure 16:
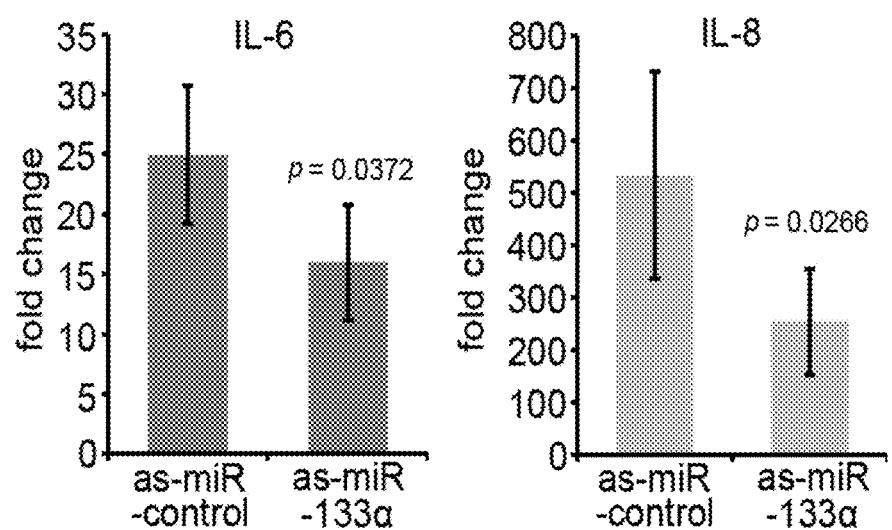
FIG. 16 shows that miR-133α silencing in human colonic epithelial NCM460 cells (by antisense miR-133α treatment) attenuated mRNA expression of the proinflammatory cytokines. IL-6 (P=0.0372) and IL-8 (P=0.0266) by by 40% and 50% respectively. This, along with the data presented in FIGS. 14 and 15 suggests that miR-133α plays an important role in regulating pro-inflammatory signaling in human colonocytes.

In order to examine the role of miR-133α in intestinal inflammation, we first examined miR-133α expression in experimental colitis models. Expression of miR-133α were increased in both TNBS- and DSS-induced experimental colitis (FIG. 12). In addition, mRNA analysis also showed an increase in miR-133α levels in colon tissues from UC patients (FIG. 13). Overexpression of miR-133α (100 nM) increased IL-8 secretion (FIG. 14) and enhanced NF-KB p65 phosphorylation, an important indicator to cellular pro-inflammatory signaling activation at both basal and stimulated conditions (FIG. 15) in vitro. On the other hand, miR-133α knock-down by antisense miR-133α reduced IL-6 and IL-8 expression in human colonocytes upon exposure to neurotensin, an important intestinal inflammation mediator (FIG. 16). These results suggest that miR-133α directly modulates NF-κB-associated intestinal inflammation in vivo and in vitro.

More importantly, antisense miR-133α treatment (20 μg/mouse) attenuated intestinal inflammation in experimental colitis when administered intracolonically. Antisense miR-133α-treated mice had lower neutrophil infiltration compared to control—treated TNBS-exposed mice. Neutrophil infiltration plays a central role in intestinal inflammation and represents the major cause of tissue damage, mucosal integrity and the resultant total histological score (FIG. 17). These suggests that miR-133α may be an important mediator for intestinal inflammation and a possible target for IBD treatment.

As demonstrated in the animal model, antisense miR-133α oligo may be administered to patients with IBD intracolonically. Higher delivery efficiency may be achieved by intravenous administration of antisense miR-133α-expressing lentivirus. Locked Nucleic acid-based miR-133 α (a more stable form) may also be used.

Cell culture. NCM460-NTR1 cells were generated from normal human colon mucosal epithelial cells, NCM460 cells (INCELL) as previously described (Bakirtzi K. Hatziapostolou M, Karagiannides et al. Neurotensin Signaling Activates MicroRNAs-21 and -155 and Akt, Promotes Tumor Growth in Mice, and Is Increased in Human Colon Tumors. Gastroenterology 2011.141:1749-1761).

Immunoblot analysis. NCM460-NTR1 cells were washed with ice-cold PBS after various treatments and incubated with radiolabelled immunoprecipitation assay buffer containing protease inhibitors, phenylmethylsulfonyl fluoride and sodium orthovanadate (Santa Cruz) for 5 min. The insoluble debris was removed by centrifugation (12,000 rpm, 15 min at 4° C.) and supernatants were analyzed by immunoblot analysis. Equal amount of cell lysates were loaded (~35 μg) and transferred to nitrocellulose membrane. The membrane was blocked with 5% non-fat dry milk (w/v) in Tris-buffered saline with 0.1% Tween 20 (TBS-T). Appropriate antibodies were incubated with the membranes overnight at 4° C., washed with TBS-T and incubated with appropriate secondary antibodies conjugated to horseradish peroxidase. Signals from target proteins were detected with SuperSignal chemiluminescent substrate (Pierce). Immunoblot bands were quantified by densitometry using Multi Gauge V3.1 (Fuji).

IL-8 ELISA. NCK/1460-NTR1 cells were stimulated with 100 nM of the proinflammatory neuropeptide neurotensin (NT) for 6 h. IL-8 in cell conditioned media was measured by Duo-Set® ELISA for IL-8 (R&D Systems) according to the manufacturer's instructions.

Experimental colitis. C57/BL6J wild-type male mice of 10-12 weeks old were purchased from The Jackson Laboratory and maintained at the animal research facility of UCLA. Animal studies were approved by the Chancellor's Animal Research Committee (ARC) of UCLA. Mice received standard pelleted chow and tap water ad libitum. Experimental colitis in C57/BL6J wild-type male mice was induced by intracolonic administration of 2,4,6-Trinitrobenzene Sulfonic Acid (TNBS, 500 mg/kg, 2 days) or Dextran Sodium Sulfate in the drinking water (DSS, 5% w/v, 5 days).

Tissues were collected for RNA and protein analysis after each treatment. Antisense miR-133α treatment. Forty-eight and 24 h prior to TNBS treatment, mice were administered as-miR-133α or its control (20 mg/mouse) via the intracolonic route. Acute TNBS colitis were induced by administering intracolonically TNBS. Tissues for mRNA and protein analysis were collected 48 h after colitis induction.

RNA Expression Studies from Patient Samples. RNAs from 6 normal colon tissues and 21 colon tissues from patients with ulcerative colitis were purchased from Origene (Rockville, Md.). Expression of miR-133α was determined by real-time PCR analysis.

Statistical analysis. All in vitro results were derived from at least of three sets of repeated experiments and expressed as means±SD and analyzed with Student's t-Tests. Studies in human tissues were analyzed with Two Sample t-Test (Origin 8.6 software). In all statistical comparisons, $P<0.05$ was used to indicate significant differences.

Neurotensin-Induced Tumor Formation is Regulated by Neurotensin Receptor 1 (NTR1)/microRNA-133α-Associated NTR1 Recycling Involving the Negative Regulator Zinc Finger E-Box-Binding Homeobox 1 (ZEB1)

Overview. G protein-coupled receptors (GPCRs) signaling is regulated by receptor endocytosis upon and recycling. We showed that neurotensin (NT) via its high affinity GPCR, neurotensin receptor 1 (NTR1), mediates intestinal inflammation, cell proliferation and colon cancer. MicroRNAs (miRNAs) are short inhibitory non-coding RNAs involved in different pathophysiological functions at the post-transcriptional level. We recently identified miR-133α and its downstream target, aftiphilin (AFTPH), localized in the trans-golgi network (TGN), to regulate NTR1 recycling in human colonocytes (DDW2012: Tu1823). Here we examined the mechanism by which NT regulates miR-133α and correlated miR-133α and AFTPH expression with colon cancer development in mouse xenografts and human colon tissue samples.

The genomic sequence of 2000 bp upstream to the start of miR-133α was analyzed by transcription binding site prediction software and identified a binding site for zinc finger E-box homeobox 1 (ZEB1, a negative transcriptional regulator). ZEB1 gene silencing in non-stimulated NCM460-NTR1 cells increased miR-133α (3.3±0.6 fold, p<0.05) and reduced AFTPH mRNA (27.2±0.1%, p<0.01). ChIP analysis showed that upon NT exposure ZEB1 was dissociated from the miR-133α promoter (41.0±1.7%, p<0.05 compared to non-stimulated cells). MiR-133α overexpression increased cyclin D1 expression (5.2±0.7 fold, p<0.001) in SW480 colon cancer cells. Blocking NTR1 recycling through AFTPH-localized TGN by Brefeldin A reduced NT-induced tumor colony formation (44.1±1.1%, p<0.05). MiR-133α overexpression and AFTPH gene silencing also promoted tumor growth in vitro (~2.0 fold and ~1.7 fold respectively, p<0.05) and in mouse cancer xenografts (~1.25 fold and ~1.6 fold respectively, p<0.05), while miR-133α knockdown attenuated NT-induced tumor growth (31.6%, p<0.05). MiR-133α mRNA was negatively correlated with AFTPH mRNA in human tumor samples (r=-0.8979, n=42), and well correlated with tumor stage (p<0.01).

Accordingly, NTR1 signaling modulates miR-133α/AFTPH expression through dissociation of ZEB1 from the miR-133α promoter, which promotes NTR1 recycling. NTR1/miR-133α/AFTPH interactions regulate colonic tumor growth. This is the first study providing evidence for an important role of microRNAs in regulation of GPCR recycling linked to development of colon cancer.

Methods. MiR-133α transcriptional regulation was verified by quantitative PCR, promoter-driven luciferase, promoter site-directed mutagenesis, and chromatin immunoprecipitation (ChIP) assays in human colonic epithelial cells overexpressing NTR1 (NCM460-NTR1). The association of miR-133α and AFTPH with tumor growth was examined by tumor colony formation assays and mouse xenografts using SW480 and HCT116 colon cancer cells.

Cancers

The antisense miR-133α treatment and AFTPH treatment can be used to treat, diagnose, and determine the prognosis of various types of colorectal cancers and IBD in subjects. As used herein, a subject can be a mammal. In specific embodiments, a subject s a human. The cancers include, for example, carcinomas, adenomatous polyps, adenocarcinomas, colonic carcinoids, colonic polyps, colorectal callous ademomas, colon cancer, bowel cancer, rectal cancer, carcinoid tumors, gastrointestinal stromal tumors, and lymphomas.

IBD includes, for example, Crohn's disease, ulcerative colitis, colitis, collagenous colitis, lymphocytic colitis, ischaemic colitis, diversion colitis, Behcet's disease, and indeterminate colitis.

Administrative Modalities

The antisense R-133α treatment agents and AFTPH treatment agents of the invention are administered to a subject, in accord with known methods, such as intracolonically, intravenously as a bolus or by continuous infusion over a period of time, by intramuscularly, intraperitoneally, intracerebrospinally, subcutaneously, intra-articularly, intrasynovially, intrathecally, orally, topically, or by an inhalation route. In certain aspects, the antisense miR-133α treatment agents and AFTPH treatment agents of the invention are administered to a subject with cancer. In certain aspects, the antisense miR-133α treatment agents and AFTPH treatment agents of the invention are administered to a subject with CRC. In certain aspects, the antisense miR-133α treatment agents and AFTPH treatment agents of the invention are administered to a subject with triple negative IBD. Intravenous or intracolonic administration of the antibody is preferred.

Combination Therapy

In some embodiments the antisense miR-133α treatment and/or AFTPH treatment is used in combination with one or more additional therapeutic agents, e.g. a chemotherapeutic agent. In certain embodiments, the chemotherapeutic agent is selected from fluorouracil (e.g., Adrucil®, Efudex®, and Fluoroplex®), bevacizumab, irinotecan hydrochloride (e.g., Camptosar®), capecitabine (e.g., Xeloda®), cetuximab (e.g., Erbitux®), oxaliplatin (e.g., Eloxatin®), leucovorin calcium (e.g., Wellcovorin®), oxaliplatin, panitumumab (e.g., Vectibix®), regorafenib (e.g., Stivara®), capecitabine (e.g., Xeloda®), and zeb-aflibercept (e.g., Zaltrap®). In certain embodiments, the chemotherapeutic agent is a chemotherapeutic drug combination treatment. In specific embodiments, the chemotherapeutic drug combination is capox (i.e., capecitabine and oxaliplatin), folfiri (i.e., leucovorin calcium, fluorouracil, and irinotecan hydrochloride), folfiri-bevacizumab (i.e., leucovorin calcium, fluorouracil, irinotecan hydrochloride, and bevacizumab), folfiri-cetuximab (i.e., leucovorin calcium, fluorouracil, irinotecan hydrochloride, and cetuximab), folfox (i.e., leucovorin calcium, fluorouracil, and oxaliplatin), or xelox (i.e., capecitabine and oxaliplatin).

Non-limiting examples of DNA damaging chemotherapeutic agents that can be used herein include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication that can be used herein include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and other inhibitors of proteins or enzymes known to be upregulated, over-expressed or activated in cancers, the inhibition of which downregulates cell replication.

In some embodiments, the antibodies of the invention can be used prior to, concurrent with, or after treatment with any of the chemotherapeutic agents described herein or known to the skilled artisan at this time or subsequently.

In some embodiments the antisense miR-133α antibody molecule thereof is used in combination with one or more additional therapeutic agents, e.g. antibiotic(s), anti-inflammatory(ies), anti-diarrheals, laxatives, pain relievers, iron supplements, aminosalicylate(s), steroids, corticosteroid(s), immune modifier(s), immunosupressor(s), anti-CD52 agents, biologic therapy(ies), vitamin B-12 shots, surgery, and nutritional plans. In certain embodiments, the anti-inflammatory(ies) is selected from a group comprising sufasalazine, mesalamine, NSAIDs, ImSAIDs, and corticosteroids. In certain embodiments, the immunosupressor(s) is selected from a group comprising zathioprine, mercaptopurine, infliximab, adalimumab, certolizumab pegol, methodtrexate, cyclosporine, natalizumab, cyclosporine, and tacrolimus. In certain embodiments, the antibiotic(s) is selected from a group comprising metronidazol and ciprofloxacin. In certain embodiments, the anti-CD52 agent is alemtuzumab.

Efficacy of Methods Described Herein

In certain aspects of this invention, efficacy of antisense miR-133α therapy is measured by decreased serum concentrations of tumor specific markers, increased overall survival time, decreased tumor size, cancer remission, decreased metastasis marker response, and decreased chemotherapy adverse affects.

In certain aspects of this invention, efficacy is measured with companion diagnostic methods and products, Companion diagnostic measurements can be made before, during, or after antisense miR-133α treatment.

In certain aspects of this invention, efficacy of AFTPH therapy is measured by decreased serum concentrations of tumor specific markers, increased overall survival time, decreased tumor size, cancer remission, decreased metastasis marker response, and decreased chemotherapy adverse affects.

In certain aspects of this invention, efficacy is measured with companion diagnostic methods and products. Companion diagnostic measurements can be made before, during, or after AFTPH treatment.

Companion Diagnostics

In other embodiments, this disclosure relates to companion diagnostic methods and products comprising antisense miR-133α. In one embodiment, the companion diagnostic method and products can be used to monitor the treatment of CRC or IBD, specifically adenocarcinomas and colitis, as described herein. In some embodiments, the companion diagnostic methods and products include molecular assays to measure levels of proteins, genes or specific genetic mutations. Such measurements can be used, for example, to predict whether antisense miR-133α therapy will benefit a specific individual, to predict the effective dosage of antisense miR-133α therapy, to monitor antisense miR-133α therapy, adjust antisense miR-133α therapy, tailor the antisense miR-133α therapy to an individual, and track cancer progression and remission.

In some embodiments, the companion diagnostic can be used to monitor a combination therapy comprising an antisense miR-133α treatment.

In some embodiments, the companion diagnostic can include an antisense miR-133α oligonucleotide described herein.

In some embodiments, the companion diagnostic can be used before, during, or after antisense miR-133α therapy.

In other embodiments, this disclosure relates to companion diagnostic methods and products comprising AFTPH. In one embodiment, the companion diagnostic method and products can be used to monitor the treatment of CRC or IBD, specifically adenocarcinomas and colitis, as described herein. In some embodiments, the companion diagnostic methods and products include molecular assays to measure levels of proteins, genes or specific genetic mutations. Such measurements can be used, for example, to predict whether AFTPH therapy will benefit a specific individual, to predict the effective dosage of AFTPH therapy, to monitor AFTPH therapy, adjust AFTPH therapy, tailor the AFTPH therapy to an individual, and track cancer progression and remission.

In some embodiments, the companion diagnostic can be used to monitor a combination therapy with AFTPH.

In some embodiments, the companion diagnostic can include AFTPH described herein.

In some embodiments, the companion diagnostic can be used before, during, or after AFTPH therapy.

Articles of Manufacture

In other embodiments, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline. Ringer's solution and dextrose solution. It may further include other materials desirable from a commercial and user standpoint, including other buffers, diluents, filters, needles, syringes, and package inserts with instructions for use.

EXAMPLES

Example 1

NT-Induced miR-133α Upregulation is Involved in NTR1 Recycling

We have previously shown that NT induces the differential expression of microRNAs in human colonocytes NT (Bakirtzi, K., et al., 2011. Neurotensin Signaling Activates MicroRNAs-21 and -155 and Akt, Promotes Tumor Growth in Mice, and Is Increased in Human Colon Tumors. *Gastroenterology* 141:1749-1761,e1741) within a time period that coincides with NTR1 internalization and recycling (Law, I. K. M., et al., 2012, Neurotensin-induced proinflammatory signaling in human colonocytes is regulated by beta-arrestins and endothelin-converting enzyme-dependent endocytosis and re-sensitization of NT receptor 1. *Journal of Biological Chemistry*). Therefore, we investigated whether the NT—up-regulated microRNAs (miRs: 140, 21, 210, 155, 133α, 23α, 23β, 331-5p) (Bakirtzi, K., et 2011. Neurotensin Signaling Activates MicroRNAs-21 and -155 and Akt, Promotes Tumor Growth in Mice, and Is Increased in Human Colon Tumors. *Gastroenterology* 141: 1749-1761.e1741) contribute to NTR1 internalization and recycling.

Figure 2:
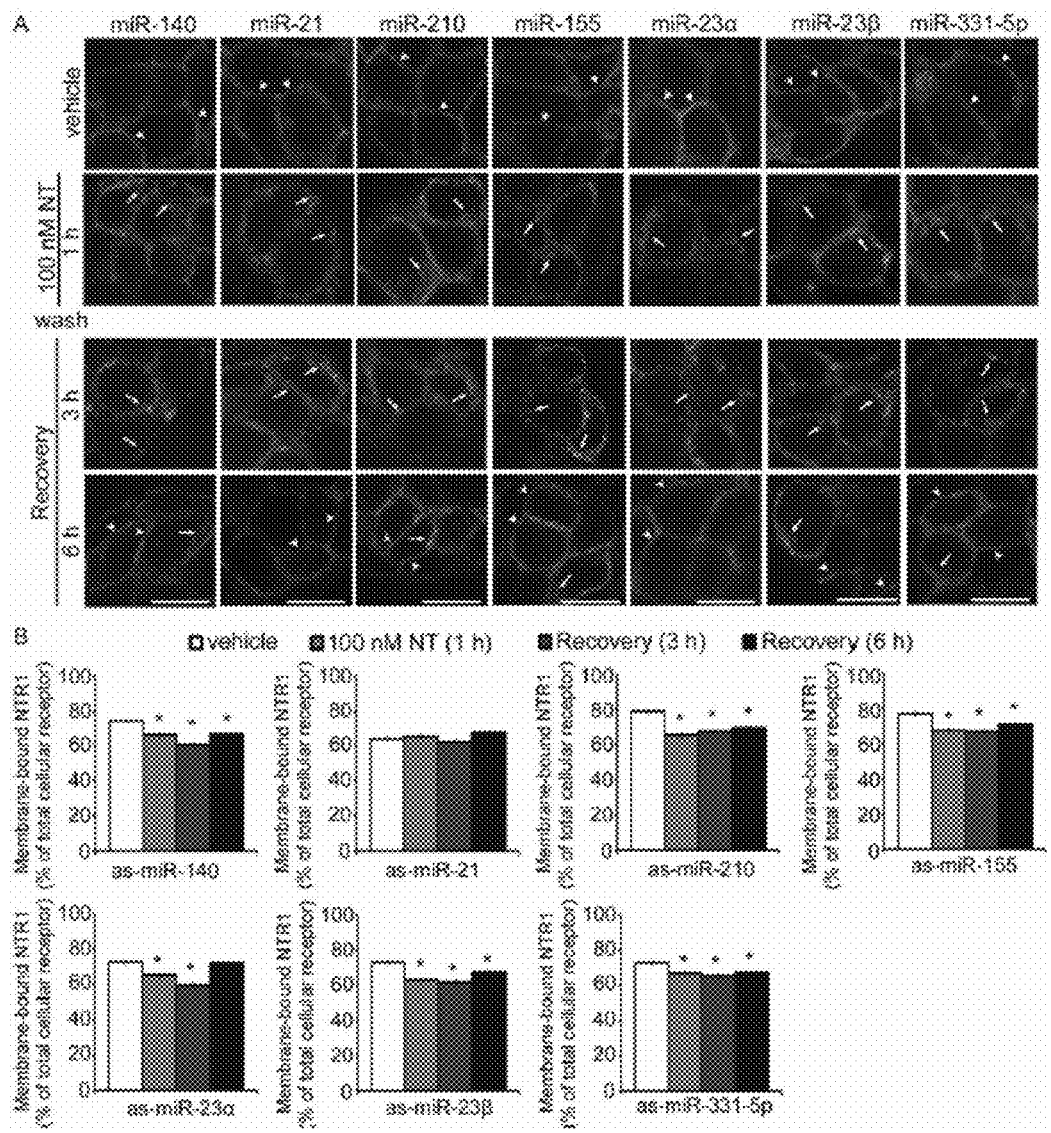
FIG. 2A-B shows downregulation of miRs: 140, 21, 210, 155, 23α, 23 beta (β), 331-5p do not affect NTR1 recycling.

NCM460-NTR1 cells transfected with antisense microRNAs were exposed to 100 nM NT for 1 h, followed by washing and replenishing with NT-free medium for 3-6 h to allow NTR1 recycling, Our results show that NT induced NTR1 endocytosis that was unaffected by any anti-miR treatment (FIG. 1A and FIG. 2). However, antisense miR-133α treatment caused a prolonged (at least 6 h) retention of NTR1 within intracellular vesicles, indicating an inhibition of recycling (FIG. 1A). Antisense miR-331-5p and 210 also caused delayed recycling, but much less pronounced compared to antisense miR-133α (FIG. 2B). In unstimulated cells, 80.0±0.82% of total cellular NTR1 was present at the plasma membrane.

NT exposure (1 h) reduced membrane-localized NTR1 in both control miR-transfected and antisense miR-133α-transfected NCM460-NTR1 cells (65.2±1.87% and 62.3±1.41% respectively). However, NTR1 levels at the plasma membrane were higher in cells transfected with control microRNAs after 3 h (73.9±221%) and 6 h (78.3±0.89%) in NT-free medium compared to antisense miR-133α-transfected cells 3 h (61.6±1.25%) and 6 hr (59.2±2.06%) after recovery (FIG. 1B, p<0.05).

Figure 3:
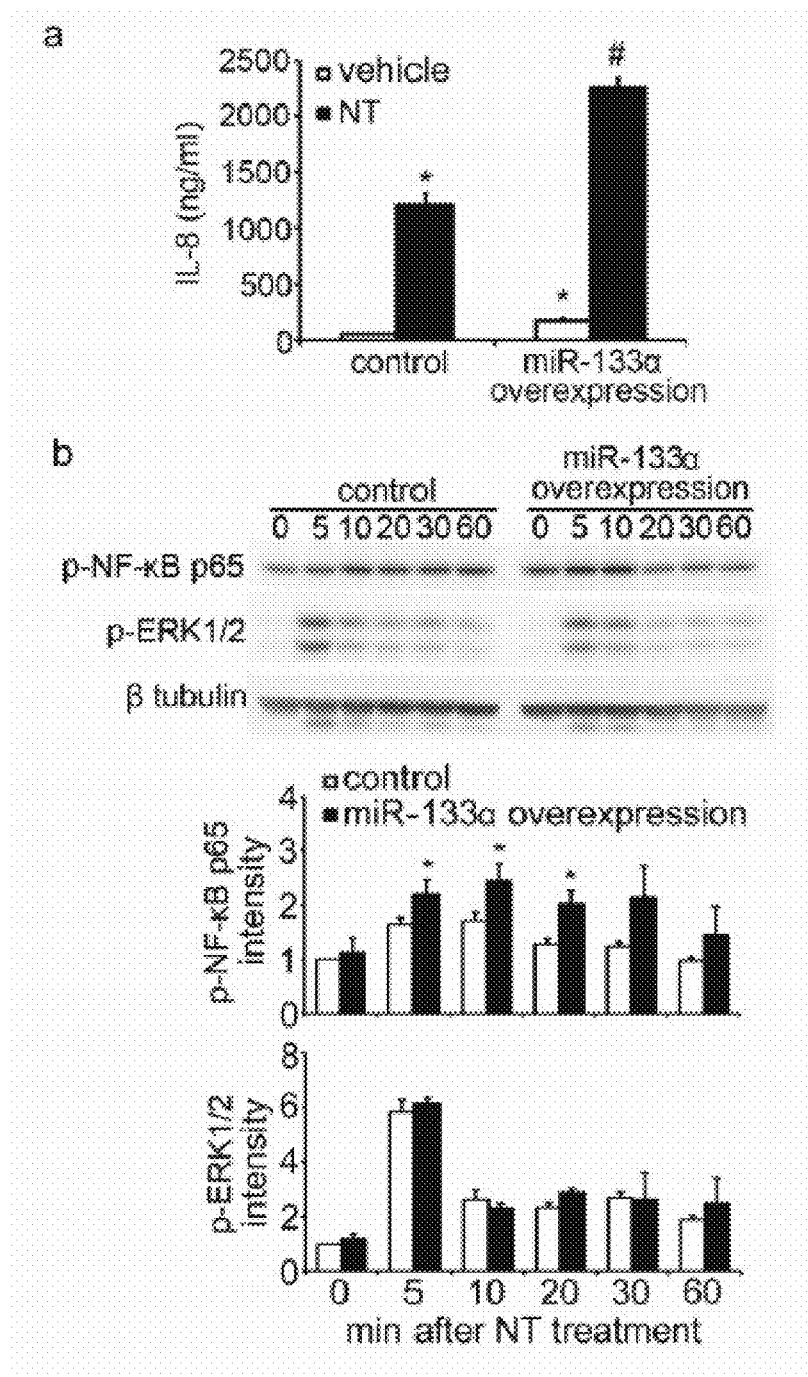
FIG. 3A-B shows overexpession of miR-133α enhances NT-Induced NF-kappa (κ) B signaling.

MiR-133α overexpression in NCM460-NTR1 cells also increased both basal IL-8 secretion (FIG. 3A) and NT-stimulated NF-κB p65 activation, but not ERK1/2 phosphorylation (FIG. 3B), supporting the hypothesis that enhanced receptor recycling promotes NT-induced cell signaling (Law, I. K. M., et al., 2012. Neurotensin-induced proinflammatory signaling in human colonocytes is regulated by beta-arrestins and endothelin-converting enzyme-dependent endocytosis and re-sensitization of NT receptor 1. *Journal of Biological Chemistry*).

Example 2

MiR-133α Directly Regulates AFTPH Expression Through Binding its 3' UTR in Colonic Epithelial Cells MicroRNAs act as gene-silencers by inducing the degeneration of mRNA transcripts through their binding to the 3' UTRs of the target genes (McKenna, et al., 2010. MicroRNAs control intestinal epithelial differentiation, architecture, and barrier function. *Gastroenterology* 139:1654-1664, 1664 e1651). Therefore, we next searched for genes with possible miR-133α binding sites in theft 3' UTRs.

In silico search using 3 online databases: TargetScanHuman; miRBase and PicTar identified aftiphilin (AFTPH) with a miR-133α binding site at its 3' UTR that was highly conserved across different species (FIG. 4A). This interaction was validated experimentally in human colonocytes. Specifically, miR-133α induction by NT treatment of NCM460-NTR1 cells resulted in down-regulation of AFTPH mRNA levels and its 3' UTR-associated luciferase activity. However, this effect was lost in the presence of antisense miR-133α (FIGS. 4B and 4C). Furthermore, deletion of the miR-133α binding site in AFTPH 3' UTR blocked NT-induced downregulation of AFTPH 3' UTR luciferase activity (FIG. 4D). In addition, miR-133α overexpression in HEK293 cells reduced AFTPH-3' UTR-associated luciferase activity in the absence of NT stimulation (FIG. 4E).

Accordingly, NT suppressed AFTPH mRNA levels through induction of miR-133α expression in colonocytes.

Example 3

Trans-Golgi Network (TGN)-Localized AFTPH Expression Modulates NT-miR133α-Regulated NTR1 Recycling AFTPH is a 936 amino acid protein with binding motifs for clathrin (Dell'Angelica, E. C., 1998. Association of the AP-3 adaptor complex with clathrin. *Science* 280:431-434), adaptor protein-1 (AP-1) and AP-2 (Mattera, R.; et al., 2004. Definition of the consensus motif recognized by gamma-adaptin ear domains. *J Biol Chem* 279:8018-8028), key mediators of endocytosis and exocytosis. Endogenous AFTPH was prominently colocalized with the TGN marker TGN38 in NCM460-NTR1 cells (FIG. 5A), in agreement with previous observations in neurons (Burman, J. L., et al., 2005. Aftiphilin is a component of the clathrin machinery in neurons. *FEBS Lett* 579:2177-2184), and was partially colocalized with NTR1 in human NCM460-NTR1 colonocytes (FIG. 5B).

To investigate the role of AFTPH in NT-induced NTR1 internalization and recycling, AFTPH expression in NCM460-NTR1 cells was knocked down by AFTPH gene silencing. Cells were stimulated with NT for 1 h, and recovered in NT-free medium for 3 h and 6 h to assess receptor endocytosis and recycling.

Figure 6:
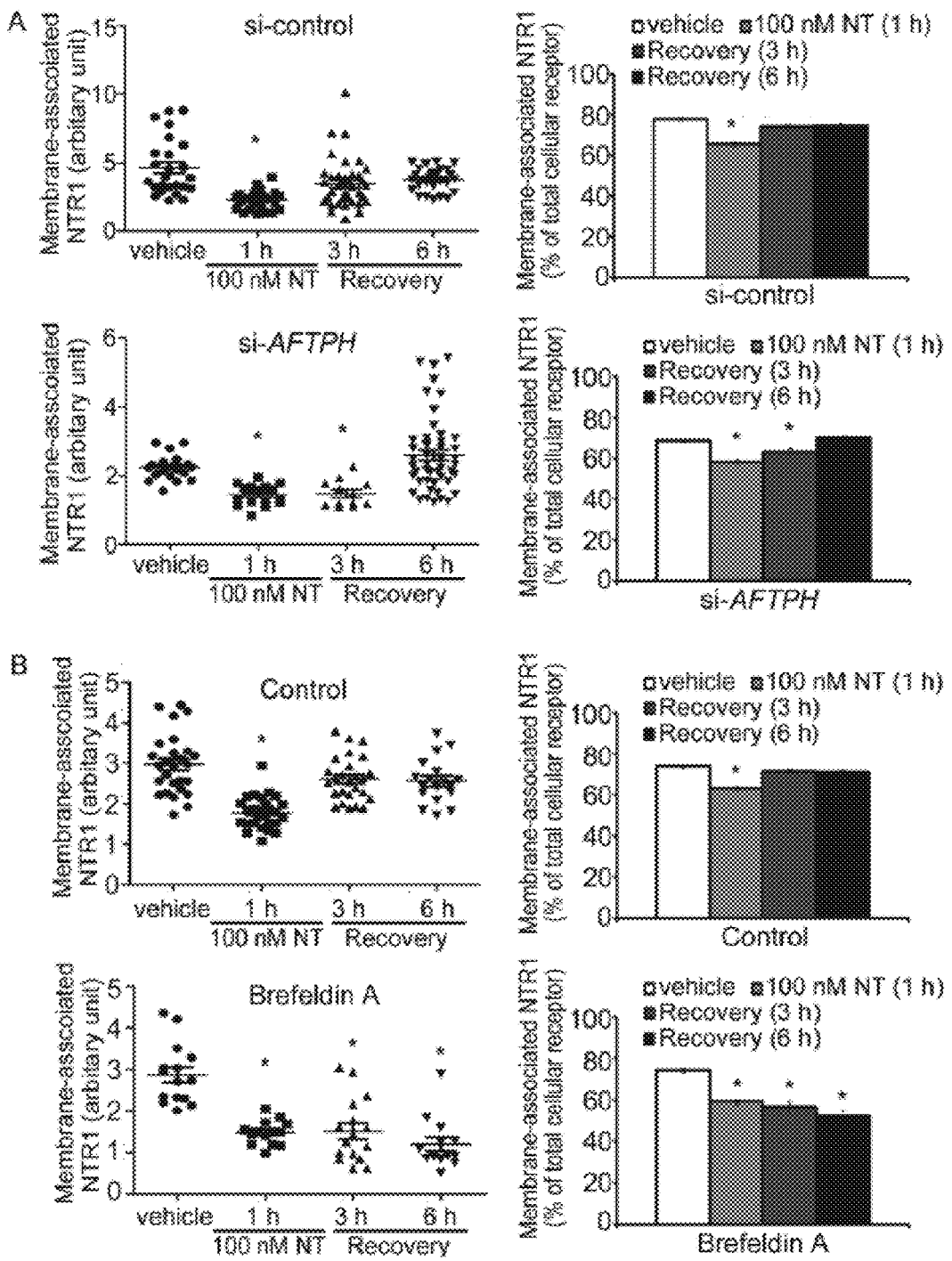
FIG. 6A-B shows that TGN-localized AFTPH gene silencing promotes NTR1 recycling.

AFTPH knockdown enhanced the recycling efficiency of internalized NTR1 back to plasma membrane after NT exposure from 68.8±0.76% (vehicle) to 70.0±1.14% (6h after NTR1 recovery); when compared to si-control-transfected cells (78.1±1.08% in vehicle control treatment and 74.6±1.73% 6 hr after NTR1 recovery) (FIG. 5C and FIG. 6).

The physiological importance of the TGN to NTR1 recycling was tested by treating NT-stimulated NCM460-NTR1 cells with 10 nM Brefeldin A; a TGN transport inhibitor (Misumi, Y., et al., 1986. Novel blockade by brefeldin A of intracellular transport of secretory proteins in cultured rat hepatocytes, *J Biol Chem* 261:11398-11403; Fujiwara, T., et al., 1988. Brefeldin A causes disassembly of the Golgi complex and accumulation of secretory proteins in the endoplasmic reticulum. *J Biol Chem* 263:18545-18552; Lippincott-Schwartz, J., et al., 1989. Rapid redistribution of Golgi proteins into the ER in cells treated with brefeldin A:

evidence for membrane cycling from Golgi to ER. *Cell* 56:801-813), during NTR1 recovery to the plasma membrane. In the presence of Brefeldin A, NTR1 did not recycle to the plasma membrane at 3 h (57.0±2.95%) and 6 h (52.1±2.89%) after NT stimulation (59.4±1.27%. FIG. 5D and FIG. 6B).

Example 4

Zinc Finger E-Box Binding Homeobox 1 (ZEB1) is a Negative Transcription Regulator of miR-133α

To examine the molecular mechanism of NT-induced miR-133α up-regulation, the genomic sequence of 2000 bp upstream to the transcription start site (TSS) of miR-133α was analyzed by online transcription binding site prediction software, Transcription Element Search System (TESS). A transcription binding site of zinc finger E-box homeobox 1 (ZEB1) was found upstream to miR-133α (FIG. 7A).

We next knocked down ZEB1 expression by siRNA in NCM-460-NTR1 cells and exposed them to 100 nM NT (1 h). In cells transfected with scrambled siRNA, miR-133α levels were increased after NT exposure, but after ZEB1 knockdown, basal miR-133α levels in the ZEB1-downregulated group were significantly higher compared to control (FIG. 7B, P<0.05). However, NT failed to increase miR-133α expression in ZEB1-silenced cells (FIG. 7B), In addition, basal AFTPH 3' UTR-associated luciferase activity (FIG. 7C) and transcription levels (FIG. 7D) were reduced significantly in ZEB1-silenced cells compared to cells transfected with scrambled siRNA (P<0.05), However, there was no significant reduction in luciferase activity or transcription levels after NT exposure (FIGS. 7C and 7D).

Chromatin-immunoprecipitation (ChIP) of the nuclear extracts from control and NT-exposed cells with a ZEB1 antibody showed reduced ZEB1 binding after NT stimulation (FIG. 7E), Moreover, miR-133α promoter-driven luciferase activity was increased by NT in control, but not in ZEB1 gene-silenced cells (FIG. 7F), or in cells transfected with a miR-133α promoter with deleted ZEB1 binding site (FIG. 7G).

Therefore, ZEB1 acts as a negative transcription regulator in NT-associated miR-133α transcription.

Example 5

NT-Induced miR-133α Up-Regulation Promotes Tumor Growth In Vitro and In Vivo

Mir-133α has been associated with cancer growth, while NT/NTR1 coupling promotes colon tumor development (Bakirtzi, K., et al., 2011. Neurotensin Signaling Activates MicroRNAs-21 and -155 and Akt, Promotes Tumor Growth in Mice, and Is Increased in Human Colon Tumors. *Gastroenterology* 141:1749-1761.e1741; Bugni, J. M., et al., 2012. The neurotensin receptor-1 promotes tumor development in a sporadic but not an inflammation-associated mouse model of colon cancer. *Int J Cancer* 130:1798-1805).

To examine the importance of miR-133α in NT-induced colon tumor development, immunodeficient nude (nu/nu) mice were inducted with HCT-116 and SW480 cells, which express endogenous NTR1 (Bakirtzi, K., et al., 2011. Neurotensin Signaling Activates MicroRNAs-21 and -155 and Akt, Promotes Tumor Growth in Mice, and Is Increased in Human Colon Tumors. *Gastroenterology* 141:1749-1761.e1741), Mice were monitored for tumor growth after NT treatment in the presence of antisense scrambled miR (as-miR-control) and antisense miR-133α (as-miR-133α).

NT treatment significantly exacerbated tumor growth in both xenograft models after the second dose was administered to both NT-treated and as-miR-control-treated mice (FIG. 8A, p<0.05). Furthermore, intratumoral injection of antisense miR-133α suppressed NT-induced tumor growth after three doses of treatment (FIG. 8A, P<0.05) in both models when compared to those in the untreated mice.

Furthermore, antisense miR-133α treatment inhibited NT-induced AFTPH mRNA reduction and IL-8 mRNA expression in tumors (FIG. 8B, P<0.05).

Figure 9:
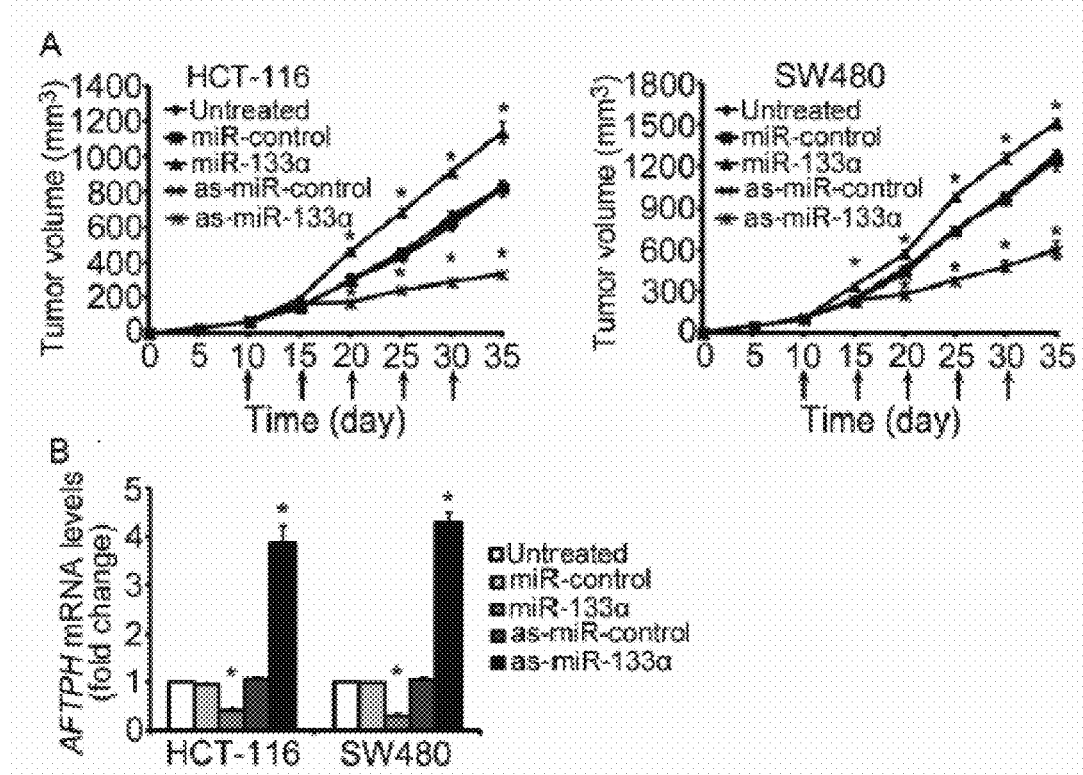
FIG. 9A-B shows that MiR-133α plays a central role in tumor growth in vivo.

Similar observations were made in xenograft models of direct miR-133α expression regulation without NT treatment in tumors. Tumor-injected mice treated with miR-133α precursor (miR-133α) showed increased tumor growth and reduced AFTPH expression in tumors (FIGS. 9A and 9B, P<0.05).

Example 6

AFTPH Acts as a Tumor Suppressor Gene in Colon Cancer

In addition to the role of NT-miR-133α pathway in colon oncogenesis, we also examined the potential function of TGN-localized AFTPH in colon cancer in vitro and in vivo.

Figure 11:
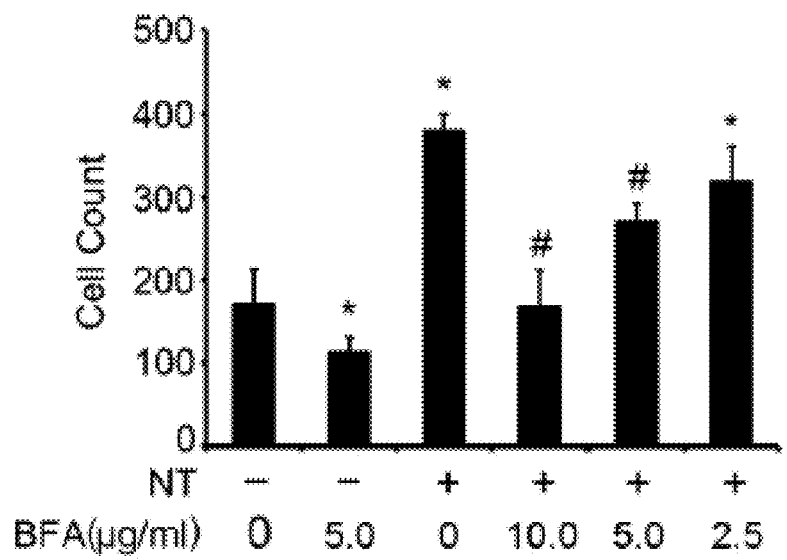
FIG. 11 shows that Brefeldin A attenuates colony formation in vitro. Anchorage-independent colony formation of untreated or Brefeldin A-treated (2.5 µg/ml, 5 µg/ml, 10 µg/ml) SW480 cells. *P<0.05 when compared to vehicle treatment; *P<0.05 when compared to NT treatment.

AFTPH gene-silencing resulted in increased HCT-116 and SW480 colony formation (FIG. 8C, P<0.05) and invasiveness (FIG. 8D, P<0.05). Accordingly, pharmacological inhibition of TGN function by Brefeldin A inhibited SW480 cell growth (FIG. 11, P<0.05). More importantly, in vivo AFTPH gene-silencing exacerbated tumor growth after one dose of treatment (FIG. 8E, P<0.05).

Taken together, these data suggest that AFTPH has a tumor suppressive function in colon cancer.

Example 7

Deregulation of NTR1/miR-133α/AFTPH Pathway in Different Stages of Human Colon Cancers NT/NTR1-induced proinflammatory responses have oncogenic functions in colon cancer (Bakirtzi, K., et al., 2011. Neurotensin Signaling Activates MicroRNAs-21 and -155 and Akt, Promotes Tumor Growth in Mice, and Is Increased in Human Colon Tumors. *Gastroenterology* 141: 1749-1761.e1741). Thus, in addition to the in vitro and in vivo relevance of the NTR1/miR-133α/AFTPH, we also examined whether this pathway was deregulated in human colon cancer tissues.

Importantly, miR-133α levels were significantly increased in human colon cancer tissues (FIG. 10A, P=0.000006) while AFTPH levels were reduced (FIG. 10B, P=0.00023), consistent with the results obtained from mouse colon cancer xenografts. Furthermore, there was a high degree of an inverse correlation between miR-133α and AFTPH expression levels (FIG. 10C, r=−0.948). In addition, increased miR-133α and decreased AFTPH mRNA expression levels were highly correlated with the severity of tumor development (FIGS. 10D and 10E).

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. AH references cited in this disclosure are incorporated by reference to the same extent as if each reference had been incorporated by reference in its entirety individually.

What is claimed is:

1. A method of treating inflammatory bowel disease in a subject in need thereof, the treatment comprising administering to the subject an effective dose of antisense miR-133α, wherein the antisense miR-133α is administered intracolonically or orally.

2. The method of claim 1, wherein the antisense miR-133α is administered intracolonically.

3. The method of claim 1, wherein the antisense miR-133α is a locked nucleic acid based miR-133α.

4. The method of claim 3, wherein the locked nucleic acid based miR-133α is administered intracolonically.

5. The method of claim 1, wherein the inflammatory bowel disease is selected from a group comprising Crohn's disease, ulcerative colitis, colitis, collagenous colitis, lymphocytic colitis, ischaemic colitis, diversion colitis, Behcet's disease, and indeterminate colitis.

6. The method of claim 1, wherein the subject is a mammal.

7. The method of claim 6, wherein the subject is a human.

8. The method of claim 1, wherein the antisense miR-133α comprises covalent internucleoside linkages.

9. The method of claim 1, wherein the dose is effective to reduce intestinal inflammation.

10. The method of claim 1, wherein the inflammatory bowel disease is ulcerative colitis.

11. The method of claim 1, wherein the inflammatory bowel disease is Crohn's disease.

12. The method of claim 1, wherein the antisense miR-133α is administered orally.

13. The method of claim 3, wherein the locked nucleic acid based miR-133α is administered orally.

* * * * *